US012678414B2

(12) United States Patent
Ridden et al.

(10) Patent No.: US 12,678,414 B2

(45) **Date of Patent: *Jul. 14, 2026**

(54) COMPOSITIONS FOR TREATMENT OF FUNGAL NAIL INFECTIONS

(71) Applicant: Blueberry Therapeutics Limited, Macclesfield (GB)

(72) Inventors: John Ridden, Macclesfield (GB); Christine Caroline Ridden, Macclesfield (GB); David Cook, Macclesfield (GB)

(73) Assignee: Blueberry Therapeutics Limited, Macclesfield (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/088,372

(22) PCT Filed: Mar. 24, 2017

(86) PCT No.: PCT/GB2017/050852

§ 371 (c)(1),
(2) Date: Sep. 25, 2018

(87) PCT Pub. No.: WO2017/163091

PCT Pub. Date: Sep. 28, 2017

(65) Prior Publication Data

US 2020/0206160 A1 Jul. 2, 2020

(30) Foreign Application Priority Data

Mar. 25, 2016 (GB) ..................................... 1605127

(51) Int. Cl.

*A61K 31/135* (2006.01)
*A61K 9/00* (2006.01)
*A61K 47/10* (2017.01)
*A61K 47/34* (2017.01)
*A61P 31/10* (2006.01)

(52) U.S. Cl.

CPC .......... *A61K 31/135* (2013.01); *A61K 9/0014* (2013.01); *A61K 47/10* (2013.01); *A61K 47/34* (2013.01); *A61P 31/10* (2018.01)

(58) Field of Classification Search

CPC .... A61K 31/135; A61K 9/0014; A61K 47/10; A61K 47/34; A61P 31/10

See application file for complete search history.

(56) References Cited

U.S. PATENT DOCUMENTS 5,681,849 A 10/1997 Richter et al.
2002/0009491 A1 1/2002 Rothbard et al.
2003/0147925 A1 8/2003 Sawan
2005/0249818 A1* 11/2005 Sawan .................... A61P 31/10 424/618
2007/0190160 A1* 8/2007 Turos .................. A61K 9/5138 424/490
2007/0249546 A1 10/2007 Sawaya et al.
2008/0312610 A1 12/2008 Binks et al.
2010/0021530 A1 1/2010 Weinfield et al.
2012/0309843 A1 12/2012 Buyuktimkin et al.
2014/0296347 A1 10/2014 Mailland et al.
2015/0111971 A1 4/2015 Evers et al.

FOREIGN PATENT DOCUMENTS

JP 2013-515742 5/2013
JP 2015-516455 6/2015
JP 2016-507540 3/2016
JP 2016-536271 11/2016
WO WO 2013/054123 A1 4/2013
WO WO-2015/044669 4/2015
WO WO-2017/006112 1/2017

OTHER PUBLICATIONS

Tayel et al (AAPS PharmSciTech, 2013; 14(2):782-793) (Year: 2013).*
Erdal et al (Pharm Dev Technol, 2014; 19(5):565-570) (Year: 2014).*
Baraldi et al., Human nail plate modifications induced by onychomycosis: implications for topical therapy, Pharm. Res, vol. 32(5):1626-33, May 2015 (ePub Nov. 2014).
Halmy, Experience with nail lacquers containing amorolfine 5% and ciclopirox 8% in patients with onychomycosis (abstract), Journal of the Am. Acad. Dermatol, vol. 52(3):P126, Mar. 2005.
International Search Report and Written Opinion, mailed May 30, 2017, issued in corresponding International Patent Application No. PCT/GB2017/050852.
Andrews et al., Common Tinea Infections in Children, American Family Physician, vol. 77(10):1415-1420, 2008.
Behrens-Baumann et al., Benefit of Polyhexamethylene Biguanide in Fusarium Keratitis, Ophthalmic Research, vol. 48(4):171-176, Jan. 2012.
Davies-Strickleton et al., Assessment of the nail penetration of antifungal agents, with different physico-chemical properties, PLOS One vol. 15(2):e0229414, Feb. 2020.
De Paula et al., Physical and Chemical Characterization of Poly(hexamethylene biguanide) Hydrochloride, Polymers, vol. 3(2):928-941, Jun. 2011.

(Continued)

*Primary Examiner* — Rayna Rodriguez

(74) *Attorney, Agent, or Firm* — Howson & Howson LLP; Colleen M. Schaller

(57) ABSTRACT

The present invention relates to a composition for use in the treatment of a fungal infection comprising a polymer capable of forming nanoparticles and terbinafine, or derivative or salt thereof, wherein the nanoparticles are formed with and/or in the presence of terbinafine, or derivative or salt thereof, and where the composition comprises: a) a ratio of terbinafine, or derivative or salt thereof, to polymer in the range of about 1:2 to 1:4; and b) up to about 30% (v/v) alcohol. The composition is particularly suited as a topical treatment for fungal nail or skin infections. The invention also relates to methods of producing such compositions and combinations which can be used to produce said same.

11 Claims, 10 Drawing Sheets

(56) References Cited

OTHER PUBLICATIONS

Elewski et al., Efficacy, safety and tolerability of topical terbinafine nail solution in patients with mild-to-moderate toenail onychomycosis: results from three randomized studies using double-blind vehicle-controlled and open-label active-controlled designs, Journal of the European Academy of Dermatology and Venereology, vol. 27(3):287-294, Mar. 2013.
Foster et al., Epidemiologic surveillance of cutaneous fungal infection in the United States from 1999 to 2002, Journal of American Academy of Dermatology, vol. 50(5):748-752, May 2004.
Hofmueller et al., Keratomycosis refractory to common therapy due to a Coelomyceter not yet described treated successfully with PHMB in combination with systemic and local terbinafine. A case report, MYCOSES, Abstract, vol. 5(Suppl. 4):95-338, P361, Jun. 2012.
Leyden, Pharmacokinetics and pharmacology of terbinafine and itraconazole, Journal of American Academy of Dermatology, vol. 38:S42-7, May 1998.
Markova, Clinical Inquiries. What is the most effective treatment for tinea pedis (athlete's foot)?, The Journal of Family Practice, Frontline Medical Communications, vol. 51(1):15-22, Jan. 2002.
Mulder et al., Polyhexamethylene Biguanide (PHMB): An Addendum to Current Topical Antimicrobials, Wounds, vol. 19(7):173-82, Jul. 2007.
Newland et al., Update on terbinafine with a focus on dermatophytosis, Clinical, Cosmetic and Investigational Dermatology, vol. 2:49-63, Apr. 2009.
Scher et al., Onychomycosis: Diagnosis and definition of cure, Journal of American Academy of Dermatology, vol. 56(6):939-944, Jun. 2007.
Office Action issued on corresponding Japanese Patent Application No. 2018-545179, dated Feb. 16, 2021 (with English machine translation).
Baswan et al. Understanding the formidable nail barrier: A review of the nail microstructure, composition and diseases. Mycoses. May 2017;60(5):284-295 [Published Online Jan. 18, 2017].
Brown et al. Overcoming the nail barrier: A systematic investigation of ungual chemical penetration enhancement. Int J Pharm. Mar. 31, 2009;370(1-2):61-7 [Published Online Nov. 24, 2008].
Office Action dated Sep. 11, 2024 issued in Japanese Patent Application No. 2023-148797, with English translation provided by local Agent.
EPO Exam Report dated Feb. 26, 2025 for Application No. 17 715 266.7.
Ghannoum et al., Activity of TDT 067 (terbinafine in Transfersome) against agents of onychomycosis, as determined by minimum inhibitory and fungicidal concentrations. J Clin Microbiol, vol. 49(5):1716-20. Mar. 16, 2011.
Tanriverdi et al., Terbinafine hydrochloride loaded liposome film formulation for treatment of onychomycosis: in vitro and in vivo evaluation. J Liposome Res, vol. 26(2):163-73. Jul. 30, 2015.

* cited by examiner

Sample video frame

Sample video frame

Figure 9A
Figure 9B
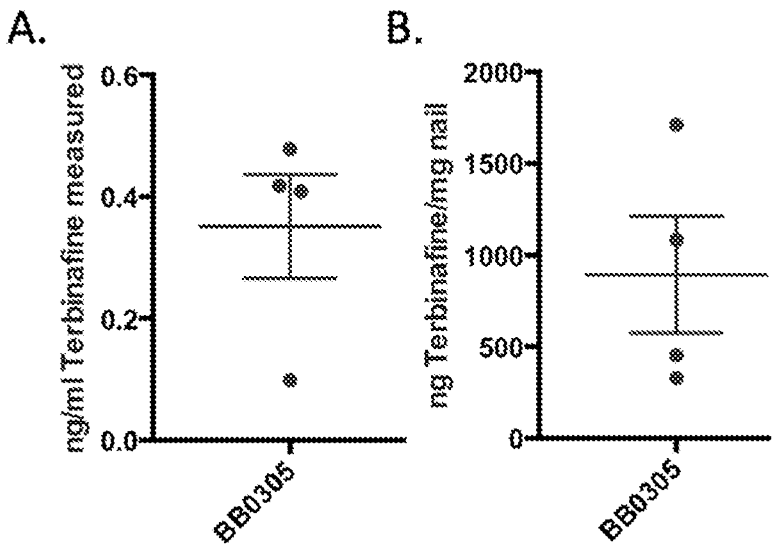
Figures 10A-10E
Figure 10A
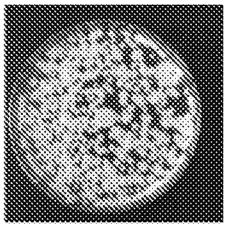
Control (ddH2O)
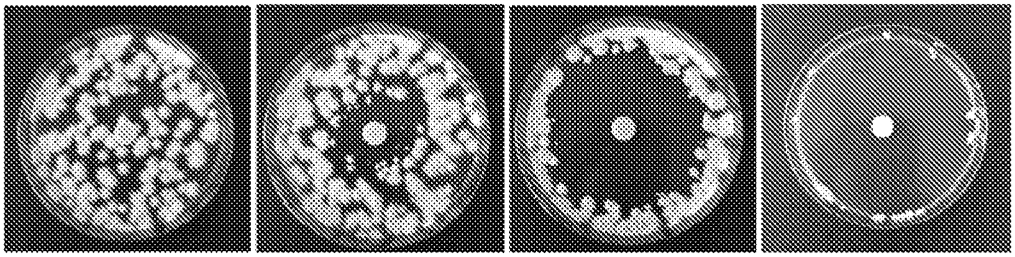
0.06μg/ml terbinafine
Figure 10B
0.60 μg/ml terbinafine
Figure 10C
6.00 μg/ml terbinafine
Figure 10D
60.0 μg/ml terbinafine
Figure 10E

COMPOSITIONS FOR TREATMENT OF FUNGAL NAIL INFECTIONS

CROSS-REFERENCE TO RELATED APPLICATIONS

This is a National Stage Entry under 35 U.S.C. 371 of International Patent Application No. PCT/GB2017/050852, filed Mar. 24, 2017. These applications are incorporated by reference herein.

TECHNICAL FIELD OF THE INVENTION

The invention relates to compositions (and methods of producing such compositions) comprising nanoparticles formed of a polymer and terbinafine. Such compositions are particularly suited, but not limited, to the treatment of fungal nail and/or skin infections.

BACKGROUND TO THE INVENTION

Fungal infections are increasingly common in both human and animals, yet the treatment of such infections remains problematic due to toxicity of the antifungal compositions, poor solubility of these compositions and the remote location of some infections which can prove difficult to reach using traditional medicinal formulations.

A broad spectrum of antifungals such as amphotericin B, hamycin, filipin and nystatin were discovered in 1960s. But due to toxicity only hamycin and nystatin are used topically and amphotericin B systemically. A breakthrough in antifungal therapy was the introduction of azoles especially ketoconazole. The major classes of antifungals currently used are polyenes, azoles allyl amines, lipopeptides, and pyrimidines. However, polyenes are toxic to mammalian cells. Azoles are well tolerated topically but have side effects when given systemically and there have been several reports of resistance to azoles. Flucytosin is the most common pyrimidine used. Whilst it has excellent tissue penetration, resistance against flucytosine can develop rapidly and produce gastro intestinal side effects. Lipopetides display low toxicity and several trials are still on going to test efficacy.

The development of new antifungals is constrained because fungi are eukaryotic and cellular targets, if disrupted, can also damage host cells. The increase in fungal infections and increase in use of antifungals has resulted in emergence of resistance among fungi. Anti-fungal resistance has high clinical impact as fungal diseases are causing an increase in morbidity and mortality of immunocompromised patients.

It is estimated that around 40% of newly discovered drugs fail due to lack of proper delivery because of aqueous solubility problems. In the case of topical delivery of drugs, the barrier properties of skin often require permeation enhancers to achieve the required dose of drugs.

Onychomycosis (more commonly known as fungal nail infection) causes nails to thicken, discolor, disfigure, and split. Without treatment, the nails can become so thick that they press against the inside of shoes, causing pressure, irritation, and pain. There are risks for further complications especially in patients with diabetes, those with peripheral vascular disease and the immunocompromised patient. Fungal nail infection may cause psychological and social problems. The incidence of fungal nail infection increases with age and has a prevalence of −30% of the over 60 s with significant incidence in Europe with even higher levels in Asia. Fungal nail infection may affect one or more toenails and/or fingernails and can completely destroy the nail if left untreated.

The current treatment for fungal nail infection is as topical nail lacquer/paint (such as amorolfine) 1-2 times per week for 6-12 months and/or oral antifungals (such as terbinafine or itraconazole). Oral antifungals can have severe side effects such as gastro-intestinal upset and can even result in liver failure. Relapse is commonly reported in 25-50% of cases and many patients will not commit to the treatment course due to predicted side effects and length of treatment time and often only when disease becomes more aggressive will treatment begin. Current oral or topical treatments can take 6-12 months to work. Oral treatments have to saturate the systemic circulation to reach the toes and the increased doses increases the risk to the gastro-intestinal and liver complications. Topical treatments are ineffective at penetrating the thickened nail and again require high dosing.

Athlete's Foot (otherwise known as ringworm of the foot, Tinea pedis or moccasin foot) is a fungal infection of the skin generally caused by fungi in the genus *Trichophyton* (most commonly *T. rubrum* or *T. mentagrophytes*). The various parasitic fungi that cause athlete's foot also can cause other skin infection such as onychomycosis and Tinea cruris. Whilst distinct from fungal nail infection, athlete's foot also has issue with compliance and duration of treatment.

Fungal keratitis is the inflammation of the cornea caused by a fungal infection. Natamycin ophthalmic suspension is often used for filamentous fungal infection, whereas Fluconazole ophthalmic solution is recommended for *Candida* infections. Amphotericin B eye drops are used for difficult to treat cases, however, these eye drops can be toxic in an individual.

Oral candidiasis is a fungal infection of the mucous membranes of the mouth by *Candida* species. It can be particularly problematic in immuno-deficient patients where it is often difficult to treat successfully.

WO2015044669 discloses a topical composition (and methods of producing such compositions) for the treatment of a fungal infection comprising a polymer capable of forming nanoparticles and an antifungal agent. WO2017/006112 discloses antifungal compositions comprising nanoparticles formed of a polymer and terbinafine, wherein the nanoparticles comprise particles in the range of 0.5 to 5 nm and/or in the range of 150 to 250 nm.

An object of the present invention is to address one or more of the above problems associated with current antifungal treatments. It is also an object of the present invention to provide a topical anti-fungal treatment. It is additionally an object of the present invention to provide a treatment which allows for better penetration of an anti-fungal agent through a number of body tissues, such as the nail and/or dermis, mucosal membranes, cornea and/or sclera. It is desirable if the present invention could be used as a single treatment for addressing both onychomycosis and tinea pedis and also be easily applied resulting in a high treatment adherence and have a low re-occurrence rate.

SUMMARY OF THE INVENTION

In accordance with a first aspect of the present invention, there is provided a composition for use in the treatment of a fungal infection comprising a polymer capable of forming nanoparticles and terbinafine, or derivative or salt thereof, wherein the nanoparticles are formed with and/or in the presence of terbinafine, or derivative or salt thereof, and where the composition comprises:

a) a ratio of terbinafine, or derivative or salt thereof, to polymer in the range of about 1:2 to about 1:4; and
b) up to about 30% (v/v) alcohol.

In accordance with an alternative first aspect of the present invention, there is provided a composition for use as a medicament, the composition comprising a polymer capable of forming nanoparticles and terbinafine, or derivative or salt thereof, wherein the nanoparticles are formed with and/or in the presence of terbinafine, or derivative or salt thereof, and where the composition comprises:

a) a ratio of terbinafine, or derivative or salt thereof, to polymer in the range of about 1:2 to about 1:4; and
b) up to about 30% (v/v) alcohol.

In accordance with a yet further alternative first aspect of the present invention, there is provided use of composition for the treatment of a fungal infection, said composition comprising a polymer capable of forming nanoparticles and terbinafine, or derivative or salt thereof, wherein the nanoparticles are formed with and/or in the presence of terbinafine, or derivative or salt thereof, and where the composition comprises:

a) a ratio of terbinafine, or derivative or salt thereof, to polymer in the range of about 1:2 to about 1:4; and
b) up to about 30% (v/v) alcohol.

In accordance with yet another further alternative first aspect of the present invention, there is provided use of a composition for the manufacture of a medicament for the treatment of a fungal infection comprising a polymer capable of forming nanoparticles and terbinafine, or derivative or salt thereof, wherein the nanoparticles are formed with and/or in the presence of terbinafine, or derivative or salt thereof, and where the composition comprises:

a) a ratio of terbinafine, or derivative or salt thereof, to polymer in the range of about 1:2 to about 1:4; and
b) up to about 30% (v/v) alcohol.

In accordance with a second aspect of the invention, there is provided a composition for use in the treatment of a fungal infection comprising:

(a) terbinafine, or derivative or salt thereof, present in an amount in the range of about 0.005% w/w to about 1% w/w;
(b) a polymer capable of forming nanoparticles and terbinafine, or derivative or salt thereof, wherein the nanoparticles are formed with and/or in the presence of terbinafine, or derivative or salt thereof and wherein the polymer is present in an amount in the range of about 0.015% w/w to about 3% w/w;
(c) alcohol at less than about 30% w/w; and
(d) water at up to about 90% w/w.

In accordance with an alternative second aspect of the present invention, there is provided a composition for use as a medicament, the composition comprising:

a) terbinafine, or derivative or salt thereof, present in an amount in the range of about 0.005% w/w to about 1% w/w;
(b) a polymer capable of forming nanoparticles and terbinafine, or derivative or salt hereof, wherein the nanoparticles are formed with and/or in the presence of terbinafine, or derivative or salt thereof and wherein the polymer is present in an amount in the range of about 0.015% w/w to about 3% w/w;
(c) alcohol at less than about 30% w/w; and
(d) water at up to about 90% w/w.

In accordance with a yet further alternative second aspect of the present invention, there is provided use of composition for the treatment of a fungal infection, said composition comprising:

a) terbinafine, or derivative or salt thereof, present in an amount in the range of about 0.005% w/w to about 1% w/w;
(b) a polymer capable of forming nanoparticles and terbinafine, or derivative or salt hereof, wherein the nanoparticles are formed with and/or in the presence of terbinafine, or derivative or salt thereof and wherein the polymer is present in an amount in the range of about 0.015% w/w to about 3% w/w;
(c) alcohol at less than about 30% w/w; and
(d) water at up to about 90% w/w.

In accordance with yet another further alternative second aspect of the present invention, there is provided use of a composition for the manufacture of a medicament for the treatment of a fungal infection comprising:

a) terbinafine, or derivative or salt thereof, present in an amount in the range of about 0.005% w/w to about 1% w/w;
(b) a polymer capable of forming nanoparticles and terbinafine, or derivative or salt hereof, wherein the nanoparticles are formed with and/or in the presence of terbinafine, or derivative or salt thereof and wherein the polymer is present in an amount in the range of about 0.015% w/w to about 3% w/w;
(c) alcohol at less than about 30% w/w; and
(d) water at up to about 90% w/w.

Such compositions of the second aspect may preferably comprise:

(a) terbinafine, or derivative or salt thereof, present at about 0.1% w/w;
(b) polymer present at about 0.3% w/w;
(c) alcohol present at about 20% w/w; and
(d) water present up to about 79.6% w/w.

Features of both the first and second aspect of the present invention my include components and quantities of those components as described below which are interchangeable with one another where appropriate.

It is preferred that the polymer comprises a linear and/or branched or cyclic polymonoguanide/polyguanidine, polybiguanide, analogue or derivative thereof. The linear and/or branched or cyclic polymonoguanide/polyguanidine, polybiguanide, analogue or derivative thereof may be according to the following formula 1a or formula 1 b, with examples provided in tables A and B below:

Formula 1a $$N\{L_1—G_1—L_2—G_2\}_nG_3$$

Formula 1b

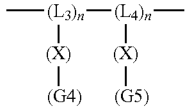

wherein:

"n", refers to number of repeating units in the polymer, and n can vary from 2 to 1000, for example from 2 or 5 to 10, 20, 30, 40, 50, 60, 70, 80, 90, 100, 150, 200, 250, 300, 350, 400, 450, 500, 600, 700, 800 or 900;

$G_1$ and $G_2$ independently represent a cationic group comprising biguanide or guanidine, wherein $L_1$ and $L_2$ are directly joined to a Nitrogen atom of the guanide. Thus, the biguanide or guanidine groups are integral to the polymer backbone. The biguanide or guanidine groups are not side chain moieties in formula 1a.

Example of Cationic Groups:

Biguanide 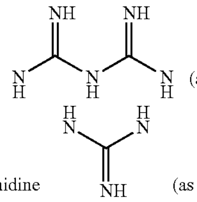 (as in PHMB) or guanidine (as in PHMG)

In the present invention, $L_1$ and $L_2$ are the linking groups between the $G_1$ and $G_2$ cationic groups in the polymer. $L_1$ and $L_2$ can independently represent an aliphatic group containing $C_1$-$C_{140}$ carbon atoms, for example an alkyl group such as methylene, ethylene, propylene, $C_4$, $C_5$, $C_6$, $C_7$, $C_8$, $C_9$ or $C_{10}$; $C_1$-$C_{10}$, -$C_{20}$, -$C_{30}$, -$C_{40}$, -$C_{50}$-$C_{60}$, -$C_{70}$, -$C_{80}$, -$C_{90}$, -$C_{100}$, -$C_{110}$, -$C_{120}$, -$C_{130}$ or -$C_{140}$, alkyl; or $L_1$ and $L_2$ can (independently) be $C_1$-$C_{140}$ (for example $C_1$, $C_2$, $C_3$, $C_4$, $C_5$, $C_6$, $C_7$, $C_8$, $C_9$ or $C_{10}$; $C_1$-$C_{10}$, -$C_{20}$, -$C_{30}$, -$C_{40}$, -$C_{50}$-$C_{60}$, -$C_{70}$, -$C_{80}$, -$C_{90}$, -$C_{100}$, -$C_{110}$, -$C_{120}$, -$C_{130}$ or -$C_{140}$), cycloaliphatic, heterocyclic, aromatic, aryl, alkylaryl, arylalkyl, oxyalkylene radicals, or $L_1$ and $L_2$ can (independently) be a polyalkylene radical optionally interrupted by one or more, preferably one, oxygen, nitrogen or sulphur atoms, functional groups as well as saturated or unsaturated cyclic moiety. Examples of suitable $L_1$ and $L_2$ are groups are listed in table A.

$L_1$, $L_2$, $G_1$ and $G_2$ may have been modified using aliphatic, cycloaliphatic, heterocyclic, aryl, alkaryl, and oxyalkylene radicals.

N and $G_3$ are preferably end groups. Typically the polymers of use in the invention have terminal amino (N) and cyanoguanidine ($G_3$) or guanidine ($G_3$) end groups. Such end groups may be modified (for example with 1,6-diaminohexane, 1,6 di(cyanoguanidino)hexane, 1,6-diguanidinohexane, 4-guanidinobutyric acid) by linkage to aliphatic, cycloaliphatic heterocyclic, heterocyclic, aryl, alkylaryl, arylalkyl, oxyalkylene radicals. In addition, end groups may be modified by linkage to receptor ligands, dextrans, cyclodextrins, fatty acids or fatty acid derivatives, cholesterol or cholesterol derivatives or polyethylene glycol (PEG). Optionally, the polymer can end with guanidine or biguanide or cyanoamine or amine or cyanoguanidine at N and $G_3$ positions or cyanoamine at N and cyanoguanidine at $G_3$ position or guanidine at N and Cyanoguanide at $G_3$ positions or $L_1$ amine at G3 and cyanoguanidine at N. G3 can be $L_1$-amine, $L_2$-cyanoguanidine or $L_2$-guanidine. Depending on the number of polymerization (n) or polymer chain breakage and side reactions during synthesis, heterogeneous mixture of end groups can arise as described above as an example. Thus, the N and G3 groups can be interchanged/present as a heterogeneous mixture, as noted above. Alternatively N and $G_3$ may be absent and the polymer may be cyclic, in which case the respective terminal $L_1$ and $G_2$ groups are linked directly to one another.

In formula 1b, X can be either present or absent. $L_3$, $L_4$ and X are as noted above for "$L_1$ or $L_2$". In Thus, $L_3$ and $L_4$ and X are the linking groups between the $G_4$ and $G_5$ cationic groups in the polymer. $L_3$ and $L_4$ and X can independently represent an aliphatic group containing $C_1$-$C_{140}$ carbon atoms, for example an alkyl group such as methylene, ethylene, propylene, $C_4$, $C_5$, $C_6$, $C_7$, $C_8$, $C_9$ or $C_{10}$; $C_1$-$C_{10}$, -$C_{20}$, -$C_{30}$, -$C_{40}$, -$C_{50}$-$C_{60}$, -$C_{70}$, -$C_{80}$, -$C_{90}$, -$C_{100}$, -$C_{110}$, -$C_{120}$, -$C_{130}$ or -$C_{140}$, alkyl; or $L_3$ and $L_4$ and X can independently be $C_1$-$C_{140}$ (for example $C_1$, $C_2$, $C_3$, $C_4$, $C_5$, $C_6$, $C_7$, $C_8$, $C_9$ or $C_{10}$; $C_1$-$C_{10}$, -$C_{20}$, -$C_{30}$, -$C_{40}$, -$C_{50}$- $C_{60}$, $C_{70}$, -$C_{80}$, -$C_{90}$, -$C_{100}$, -$C_{110}$, -$C_{120}$, -$C_{130}$ or -$C_{140}$), cycloaliphatic, heterocyclic, aromatic, aryl, alkylaryl, arylalkyl, oxyalkylene radicals, or $L_3$ and $L_4$ and X can independently be a polyalkylene radical optionally interrupted by one or more, preferably one, oxygen, nitrogen or sulphur atoms, functional groups as well as saturated or unsaturated cyclic moiety. Examples of suitable $L_3$ and $L_4$ and X are groups are listed in table B.

"$G_4$" and "$G_5$" are cationic moieties and can be same or different. At least one of them is a biguanidine moiety or carbamoylguanidine, and the other moiety may be as above (biguanidine or carbamoylguanidine) or amine. For the avoidance of doubt, in formula 1b, cationic moiety $G_4$ and $G_5$ do not contain only single guanidine groups. For example, $G_4$ and $G_5$ typically do not contain single guanidine groups. Examples of such compounds are polyallylbiguanide, poly(allylbiguanidnio-co-allylamine), poly(allylcarbamoylguanidino-co-allylamine), polyvinylbiguanide, as listed in table B.

Example of polyallylbiguanide is as shown below:

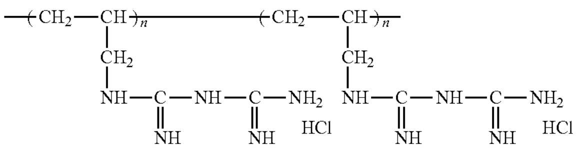 [SMILES: CCC(CNC(=N)NC(=N)N)CC(C)CNC(=N)NC(=N)N ; Cl ; Cl]

In case of polyallylbigunidine $L_3$ and $L_4$ are identical, $G_4$ and G5 are similar, thus polyallylbiguanide can be simplified as below.

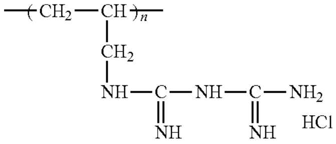

Example of poly(allylcarbamoylguanidnio-co-allylamine) is as shown below

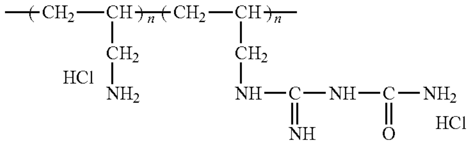 [SMILES: CCC(CN)CC(C)CNC(=N)NC(N)=O ; Cl ; Cl]

The polymers for use in the invention will generally have counter ions associated with them. Suitable counter ions include but are not limited to the following: halide (for example chloride), phosphate, lactate, phosphonate, sulfonate, amino carboxylate, carboxylate, hydroxy carboxylate, organophosphate, organophosphonate, organosulfornate and organosuflate.

Polymers for use in the invention can be either heterogeneous mixtures of polymers of different "n" number or homogenous fractions comprising specified "n" numbers purified by standard purification methods. As indicated above the polymers may also be cyclic and in addition may be branched.

Preferred numbers for "n" include 2-250, 2-100, 2-80 and 2-50.

TABLE A

| Examples of polymer analogues arising from formula 1a. | | | | |
|---|---|---|---|---|
| Name | $L_1$ | $G_1$ | $L_2$ | $G_2$ |
| Polyhexamethylene biguanide (PHMB) | $(CH_2)_6$ | Biguanide | $(CH_2)_6$ | Biguanide |
| Polyethylene biguanide (PEB) | $(CH_2)_2$ | Biguanide | $(CH_2)_2$ | Biguanide |
| Polyethylenetetramethylene biguanide | $(CH_2)_2$ | Biguanide | $(CH_2)_4$ | Biguanide |
| Polyethylene hexamethylene biguanide (PEHMB) | $(CH_2)_2$ | Biguanide | $(CH_2)_6$ | Biguanide |
| Polypropylene biguanide, Polyaminopropyl biguanide (PAPB) | $(CH_2)_3$ | Biguanide | $(CH_2)_3$ | Biguanide |
| Poly-[2-(2-ethoxy)-ethoxyethyl]-biguanide- chloride] (PEEG) | $(CH_2CH_2OCH_2CH_2OCH_2CH_2)$ | Biguanide | $(CH_2CH_2OCH_2CH_2OCH_2CH_2)$ | Biguanide |
| Polypropylenehexamethylene biguanide | $(CH_2)_3$ | Biguanide | $(CH_2)_6$ | Biguanide |
| Polyethyleneoctamethylene biguanide | $(CH_2)_2$ | Biguanide | $(CH_2)_8$ | Biguanide |
| Polyethylenedecamethylene biguanide | $(CH_2)_2$ | Biguanide | $(CH_2)_{10}$ | Biguanide |
| Polyethylenedodecamethylene biguanide | $(CH_2)_2$ | Biguanide | $(CH_2)_{12}$ | Biguanide |
| Polytetramethylenehexamethylene biguanide | $(CH_2)_4$ | Biguanide | $(CH_2)_6$ | Biguanide |
| Polytetramethylenebiguanide | $(CH_2)_4$ | Biguanide | $(CH_2)_4$ | Biguanide |
| Polypropyleneoctamethylene biguanide | $(CH_2)_3$ | Biguanide | $(CH_2)_8$ | Biguanide |
| Polytetramethyleneoctamethylene Biguanide | $(CH_2)_4$ | Biguanide | $(CH_2)_8$ | Biguanide |
| Polyhexamethylene diethylenetriamine biguanide | $(CH_2)_6$ | Biguanide | $CH_2—CH_2—NH—CH_2—CH_2$ | Biguanide |
| Polyhexamethylene guanide (PHMG) | $(CH_2)_6$ | guanidine | $(CH_2)_6$ | guanidine |
| Polyethylene guanide | $(CH_2)_2$ | guanidine | $(CH_2)_2$ | guanidine |
| Polyethylenetetramethylene guanide | $(CH_2)_2$ | guanidine | $(CH_2)_4$ | guanidine |
| Polyethylene hexamethylene guanide | $(CH_2)_2$ | guanidine | $(CH_2)_6$ | guanidine |
| Polypropylene guanide, Polyaminopropyl guanide (PAPB) | $(CH_2)_3$ | guanidine | $(CH_2)_3$ | guanidine |
| Poly-[2-(2-ethoxy)-ethoxyethyl]-guanide | $(CH_2CH_2OCH_2CH_2OCH_2CH_2)$ | guanidine | $(CH_2CH_2OCH_2CH_2OCH_2CH_2)$ | guanidine |
| Polypropylenehexamethylene guanide | $(CH_2)_3$ | guanidine | $(CH_2)_6$ | guanidine |
| Polyethyleneoctamethylene guanide | $(CH_2)_2$ | guanidine | $(CH_2)_8$ | guanidine |
| Polyethylenedecamethylene guanide | $(CH_2)_2$ | guanidine | $(CH_2)_{10}$ | guanidine |
| Polyethylenedodecamethylene guanide | $(CH_2)_2$ | guanidine | $(CH_2)_{12}$ | guanidine |
| Polytetramethylenehexamethylene guanide | $(CH_2)_4$ | guanidine | $(CH_2)_6$ | guanidine |
| Polypropyleneoctamethylene guanide | $(CH_2)_3$ | guanidine | $(CH_2)_8$ | guanidine |
| Polytetramethylene guanide | $(CH_2)_4$ | guanidine | $(CH_2)_4$ | guanidine |
| Polyhexamethylene diethylenetriamine guanide | $(CH_2)_6$ | guanidine | $CH_2—CH_2—NH—CH_2—CH_2$ | guanidine |

| Polymer | CAS Number |
|---|---|
| Polyhexamethylene biguanide | 27083-27-8 |
| hydrochloride (PHMB) | 32289-58-0 |
| Polyhexamethylene guanidine | 57028-96-3 |
| hydrochloride (PHMG) | |

-continued

| Polymer | CAS Number |
|---|---|
| Poly-[2-(2-ethoxy)-ethoxyethyl]-guanidinium-chloride] (PEEG) | 374572-91-5 |

CAS Numbers for Example Compounds Arising from Formula 1a

TABLE B

| Examples of polymer analogues arising from formula 1b. | | | | | |
|---|---|---|---|---|---|
| Name | $L_3$ | $G_4$ | $L_4$ | $G_5$ | x |
| Polyallylbiguanide | $(CH_2—CH)$ | Biguanide | $(CH_2—CH)$ | Biguanide | $CH_2$ |
| poly(allylbiguanidnio-co-allylamine) | $(CH_2—CH)$ | amine | $(CH_2—CH)$ | biguanide | $CH_2$ |
| poly(allylcarbamoyl-guanidino-co-allylamine) | $(CH_2—CH)$ | amine | $(CH_2—CH)$ | Carbamoyl guanidine | $CH_2$ |
| polyvinylbiguanide | $(CH_2—CH)$ | Biguanide | $(CH_2—CH)$ | biguanide | absent |

The polymer used may comprise linear, branched or dendrimeric molecules. The polymer may comprise a combination of linear, branched or dendrimeric molecules. The polymer may comprise one or any combination of molecules of Formula 1a or Formula 1b, for example as described above.

For example, the polymer can comprise one or more of polyhexamethylene biguanide (PHMB), polyhexamethylene monoguanide (PHMG), polyethylene biguanide (PEB), polytetramethylene biguanide (PTMB) or polyethylene hexamethylene biguanide (PEHMB). Some examples are listed in table A and B.

Thus, the polymer may comprise homogeneous or heterogeneous mixtures of one or more of polyhexamethylene biguanide (PHMB), polyhexamethylene monoguanide (PHMG), polyethylene biguanide (PEB), polytetramethylene biguanide (PTMB), polyethylene hexamethylene biguanide (PEHMB), polymethylene biguanides (PMB), poly (allylbiguanidnio-co-allylamine), poly(N-vinylbiguanide), polyallybiguanide. The most preferred polymer comprises polyhexamethylene biguanide (PHMB).

The term "terbinafine, or derivative or salt thereof" is intended to mean the pharmaceutically active substance related to terbinafine hydrochloride, which is a synthetic allylamine antifungal originally marketed under the trade name Lamisil®. The term is also intended to include pharmaceutical variations, derivatives, alternative salts, of terbinafine hydrochloride such as non-toxic organic, or inorganic, acid, or base, addition salt, in a pharmaceutically acceptable form.

The terbinafine, or derivative or salt thereof, may be present in an amount in the range of about 5 to about 1000 μg/ml. Preferably, the terbinafine, or derivative or salt thereof, may be present in the range of about 5 to about 600 μg/ml. More preferably, the terbinafine, or derivative or salt thereof, will be present in the range of about 25 to about 200 μg/ml. Even more preferably, the terbinafine, or derivative or salt thereof, will be present in the range of about 50 to about 150 μg/ml. Most preferably, the terbinafine, or derivative or salt thereof, will be present at about 100 μg/ml.

The polymer may be present in an amount in the range of about 15 to about 3000 μg/ml. Preferably, the polymer is present in the range of about 15 to about 1800 μg/ml. More preferably, the polymer will be present in the range of about 75 to about 600 μg/ml. Even more preferably, the polymer will be present in the range of about 150 to about 450 μg/ml. Most preferably, the polymer will be present at about 300 μg/ml. The polymer will preferably comprise PHMB.

The alcohol may be present in an amount in the range of about 5% to about 29% or about 30% (v/v). Preferably, the alcohol will be in an amount in the range of about 10% to about 29% or about 30% (v/v). More preferably, the alcohol will be in an amount in the range of about 20% to about 29% or about 30% (v/v). Yet more preferably, the alcohol will be in an amount up to about 25% or 23% (v/v). Most preferably, the alcohol is in an amount up to about 20% (v/v).

The alcohol will preferably comprise ethanol, although it may comprise (whether alone or in combination with) other alcohols such as methanol or propanol.

The composition may also comprise water. The water will preferably be distilled water. The water may be present in an amount in the range of about 70% to about 95% (v/v). Preferably, the water will be in an amount in the range of about 70% to about 90% (v/v). More preferably, the water will be in an amount in the range of about 70% to about 80% (v/v). Yet more preferably, the water will be in an amount over about 77% (v/v). Most preferably, the water is in an amount up to about 90% (v/v), up to about 80% (v/v) or up to about 79.6% (v/v).

The terbinafine, or derivative or salt thereof, may be present in an amount in the range of about 0.005% w/w to about 1.0% w/w. Preferably, the terbinafine, or derivative or salt thereof, may be present in the range of about 0.005% w/w to about 0.6% w/w. More preferably, the terbinafine, or derivative or salt thereof, will be present in the range of about 0.025% w/w to about 0.2% w/w. Even more preferably, the terbinafine, or derivative or salt thereof, will be present in the range of about 0.05% w/w to about 0.15% w/w. Most preferably, the terbinafine, or derivative or salt thereof, will be present at about 0.1% w/w.

The polymer may be present in an amount in the range of about 0.15% w/w to about 3% w/w. Preferably, the polymer is present in the range of about 0.15% w/w to about 1.8% w/w. More preferably, the polymer will be present in the range of about 0.75% w/w to about 0.6% w/w. Even more preferably, the polymer will be present in the range of about 0.15% w/w to about 0.45% w/w. Most preferably, the polymer will be present at about 0.3% w/w. The polymer will preferably comprise PHMB.

The alcohol may be present in an amount in the range of about 5% w/w to about 29% w/w. Preferably, the alcohol will be in an amount in the range of about 10% w/w to about 29% w/w. More preferably, the alcohol will be in an amount in the range of about 20% w/w to about 29% w/w. Yet more preferably, the alcohol will be in an amount up to about 29% w/w, more preferably up to about 25%, even more preferably up to about 23% w/w and most preferably, the alcohol is in an amount up to about 20% w/w.

The alcohol will preferably comprise ethanol, although it may comprise (whether alone or in combination with) other alcohols such as methanol or propanol.

The composition may also comprise water. The water will preferably be distilled water. The water may be present in an amount in the range of about 70% w/w to about 95% w/w. Preferably, the water will be in an amount in the range of about 70% w/w about 90% w/w. More preferably, the water will be in an amount in the range of about 70% w/w to about 80% w/w. Yet more preferably, the water will be in an amount up to about 70% w/w, more preferably up to about 77% w/w. Most preferably, the alcohol is in an amount up to about 90% w/w, up to about 80% w/w or up to 79.6% w/w.

It is preferred that the composition only comprises terbinafine, the polymer, alcohol and water. That is to say, that no further excipients or solvents are included in the composition.

The ratio of terbinafine, or derivative or salt thereof, to polymer may be about 1:3±0.75. Preferably, the ratio of terbinafine, or derivative or salt thereof, to polymer will be about 1:3±0.5. More preferably, the ratio of terbinafine, or derivative or salt thereof, to polymer will be about 1:3±0.25. Even more preferably, the ratio of terbinafine, or derivative or salt thereof, to polymer will be about 1:3±0.1. Most preferably, the ratio of terbinafine, or derivative or salt thereof, to polymer will be about 1:3.

The nanoparticles may comprise particles formed in two diametrically distinct species. This may comprise a first species in the range of 0.5 to 5 nm and a second species in the range of 50 to 350 nm.

The relative quantities of first species to the second species may be generally equal with one another, or one species may be the more prominent species within the composition.

Preferably, the particles in the first species are in the range of 0.5 to 3 nm. More preferably, the particles in the first species are in the range of 0.5 to 2.5 nm. Most preferably, the particles in the first species are in the range of 0.5 to 2 nm. Preferably, the particles in the second species are in the range of 75 to 325 nm. More preferably, the particles in the second species are in the range of 100 to 300 nm. Most preferably, the particles in the second species are in the range of 150 to 200 nm or 215 nm.

Preferably, the average size of the particles in the first species will be in the range of 0.5 to 1.5 nm. More preferably, the average size of the particles in the first species will be in the range of 0.6 to 1.4 nm. Even more preferably, the average size of the particles in the first species will be in the range of 0.7 to 1.2 nm. Most preferably, the average size of the particles in the first species will be in the region of about 0.9 nm.

Preferably, the average size of the second species of particles will be in the range of 50 to 350 nm. More preferably, the average size of the second species of particles will be in the range of 100 to 300 nm. Even more preferably, the average size of the second species of particles will be in the range of 150 to 200 nm. Most preferably, the average size of the second species of particles will be in the region of about 160 to about 176 nm.

Preferably, the average modal size of the second species of particles will be in the range of 150 to 225 nm. More preferably, the average modal size of the second species of particles will be in the range of 155 to 220 nm. Even more preferably, the average modal size of the second species of particles will be in the range of 160 to 215 nm. Most preferably, the average modal size of the second species of particles will be in the region of about 164 to about 211 nm.

The composition may comprise a topically applied composition.

It will be apparent to the skilled addressee that the composition may further comprise one or more of the following components: buffers, excipients, binders, oils, solvents, water, emulsifiers, glycerin, antioxidants, preservatives and fragrances or any additional components usually found in medicaments, and in particular topical creams and ointments. Furthermore, the composition could be in a number of forms such as a paste or a suspension. The composition may be formulated for use with a spraying device or for use in conjunction with a micro-needle array delivery system. If a micro-needle array is employed then it may be incorporated into an adhesive patch.

For certain applications, the compositions may additionally comprise a permeating agent so as to allow delivery of terbinafine agent to infected area. For example, urea can be used to allow the nanoparticles breach the nail of an individual suffering from a fungal nail infection where the infection is underneath or in the nail itself. Additionally, certain solvents may be employed so as to enable dissolution of one or more components of the composition, such as terbinafine, into solution.

The compositions of the invention may also be administered intranasally or by inhalation and may be conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoro-ethane, a hydrofluoroalkane such as 1,1,1,2-tetrafluoroethane (HFA 134A or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the composition, e.g. using a mixture of ethanol and the propellant as the solvent, which may additionally contain a lubricant, eg sorbitan trioleate. Capsules and cartridges (made, for example, from gelatin) for use in an inhaler or insufflator may be formulated to contain a powder mix of the composition of the invention and a suitable powder base such as lactose or starch.

Aerosol or dry powder formulations are preferably arranged so that each metered dose or "puff" contains at least 1 μg of the composition for delivery to the patient. It will be appreciated that the overall daily dose with an aerosol will vary from patient to patient, and may be administered in a single dose or, more usually, in divided doses throughout the day.

Alternatively, the compositions of the invention can be administered in the form of a suppository or pessary, or they may be applied topically in the form of a lotion, solution, cream, ointment or dusting powder. The composition of the invention may also be transdermally administered, for example, by the use of a skin patch. They may also be administered by the ocular route, particularly for treating diseases of the eye.

For ophthalmic use, the compositions of the invention can be formulated using nanoparticle systems or as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compositions of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compositions as herein above described can be used to treat a number of fungal infections. However, it is particularly suited to treat fungal nail infection, athlete's foot or other types of fungal skin infection/dermatophyte infections (such as ringworm of the groin (Tinea cruris), ringworm of the body (Tinea corporis), ringworm of the scalp (Tinea capitis), other "ringworm" type infections). The invention will also be suited to treating yeast infections such as, but not limited to, intertrigo, pityriasis versicolor, and thrush (*Candida albicans*). The fungal infection may comprise a dermatophytic infection. However, the present invention can also be used to treat or modulate yeast infections and/or colonisation. The composition as herein above described may be for use in the treatment or management of a fungal infection. The treatment may be a topical treatment.

Furthermore, the compositions as herein above described may be used to treat a number of fungal disorders, such as treating fungal nail infection and athlete's foot.

In accordance with a further aspect of the present invention, there is provided a method of producing a composition for use in the treatment of a fungal nail or skin infection comprising mixing, in a ratio of about 1:2 to about 1:4, a polymer capable of forming nanoparticles and terbinafine, or salt or derivative thereof, under conditions suitable to allow the formation of nanoparticles and adding up to up to about 30% (v/v) alcohol.

It is preferred that the method is used to produce a composition as described with reference to the first aspect of the invention.

Various methods may be used to form the nanoparticles and it is envisaged that the nanoparticles will be formed as a polymer and terbinafine complex. However, polymer nanoparticles may be independently formed and then incubated with terbinafine together or separately in any order. Terbinafine may be absorbed or attached to the nanoparticles in such a way so as to retain the efficacy of the antifungal agent against the fungi and the penetration enhancing effects of the nanoparticles.

In a further aspect of the present invention, there is provided a combination of:

a) a polymer capable of forming nanoparticles with terbinafine or derivative or salt thereof;

b) terbinafine, or derivative or salt thereof; and c) alcohol;

wherein the terbinafine, or derivative or salt thereof, is provided in a ratio to polymer in the range of about 1:2 to about 1:4; and the alcohol is provided in an amount of up to about 30% (v/v).

Preferably, the combination is used for producing a composition as herein above described with reference to the first and second aspects or in a method as herein above described with reference to the further aspects.

A number of techniques may be employed to further process the mixture so as to select the nanoparticles in the required size ranges, such as centrifugation, electrophoretic, chromatographic or filtration methods. The measurement of the size/diameter of the nanoparticles is preferably conducted using dynamic light scattering analysis.

The method may further comprise formulating the composition into a topical medicament.

Again, it will be apparent that the method will be employed to produce a composition as herein above described.

In a yet an additional aspect of the present invention, there is provided a combination of a composition as herein above described and a micro-needle array for use in the treatment of a fungal nail infection. The micro-needle array may be incorporated into an adhesive patch. The micro-needles may be less than 2 mm in length. More preferably, the micro-needles are less than 1.5 mm in length. Most preferably, the micro-needles are less than 1 mm in length. Preferably, less than 500 μm of the micro-needles are inserted into the skin. More preferably, less than 400 μm of the micro-needles are inserted into the skin. Most preferably, about 300 to 200 μm of the micro-needs are inserted into the skin. Preferably, the micro-needles administer the composition to the dermis and/or epidermis.

DETAILED DESCRIPTION OF THE INVENTION

Embodiments of the present invention will now be described, by way of example only, with reference to the following experiments and accompanying figures, in which.

Figure 2A:
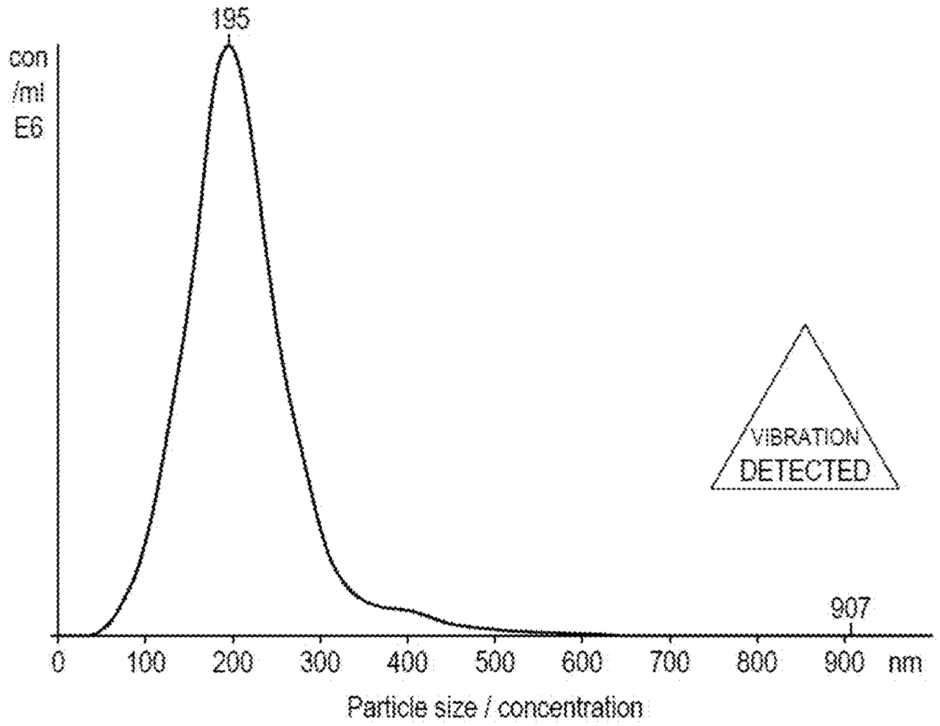
Figure 2B:
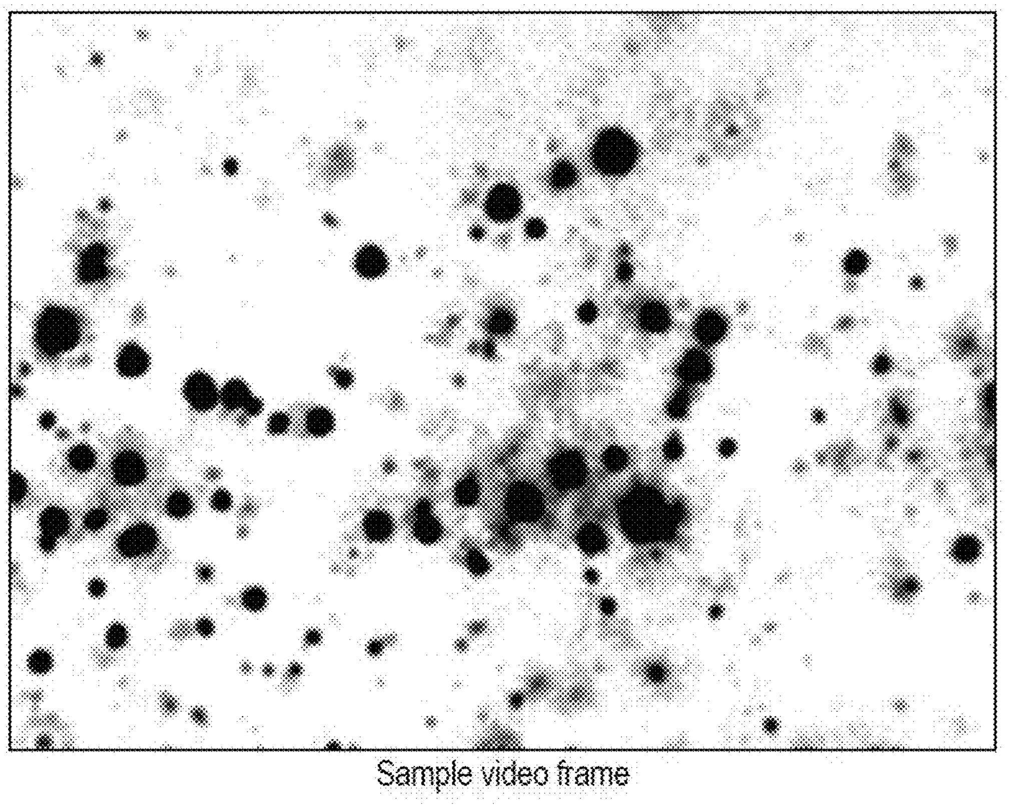
Figure 3:
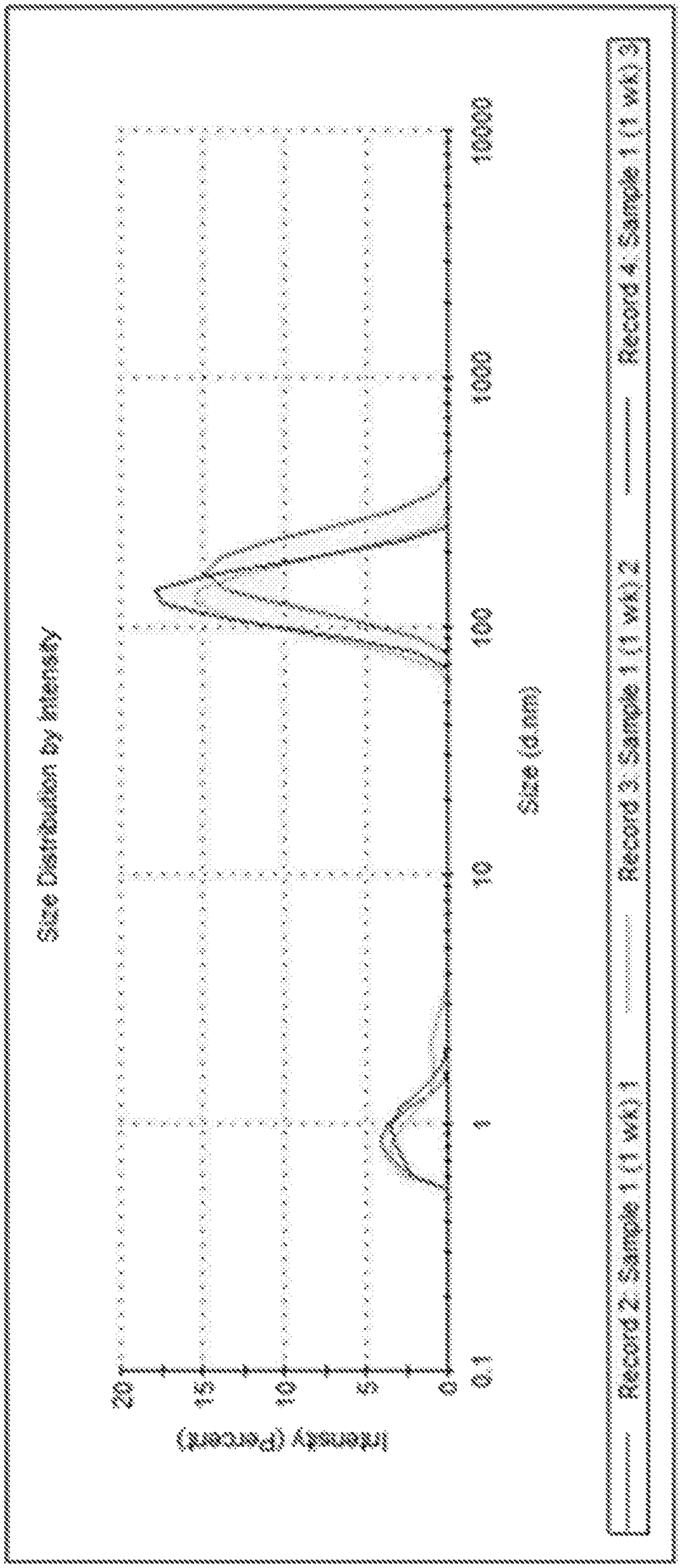
Figure 4B:
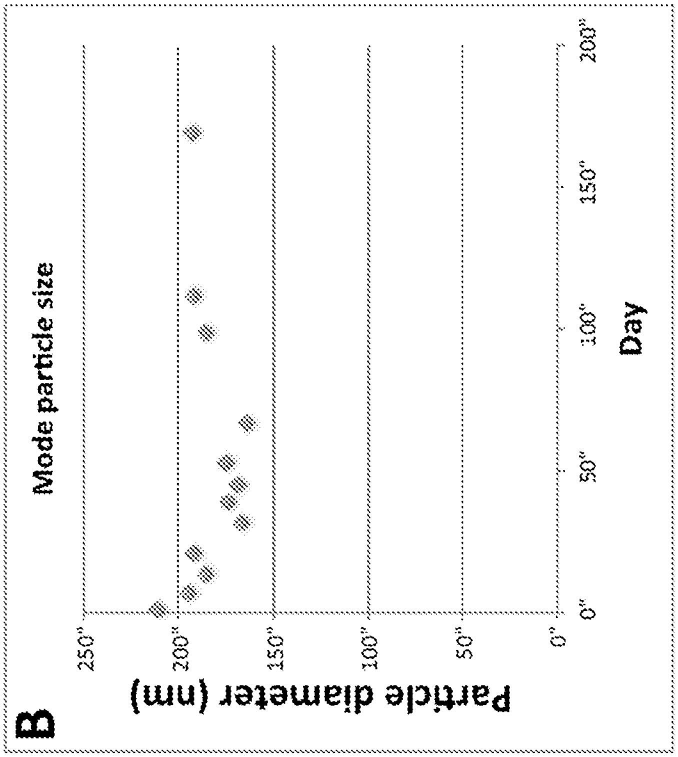
Figure 4A:
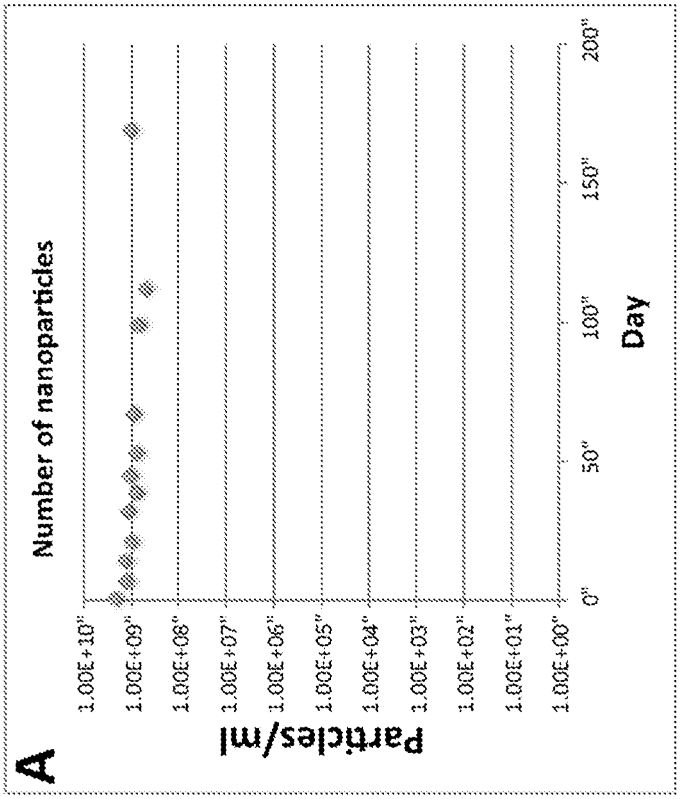
Figure 5:
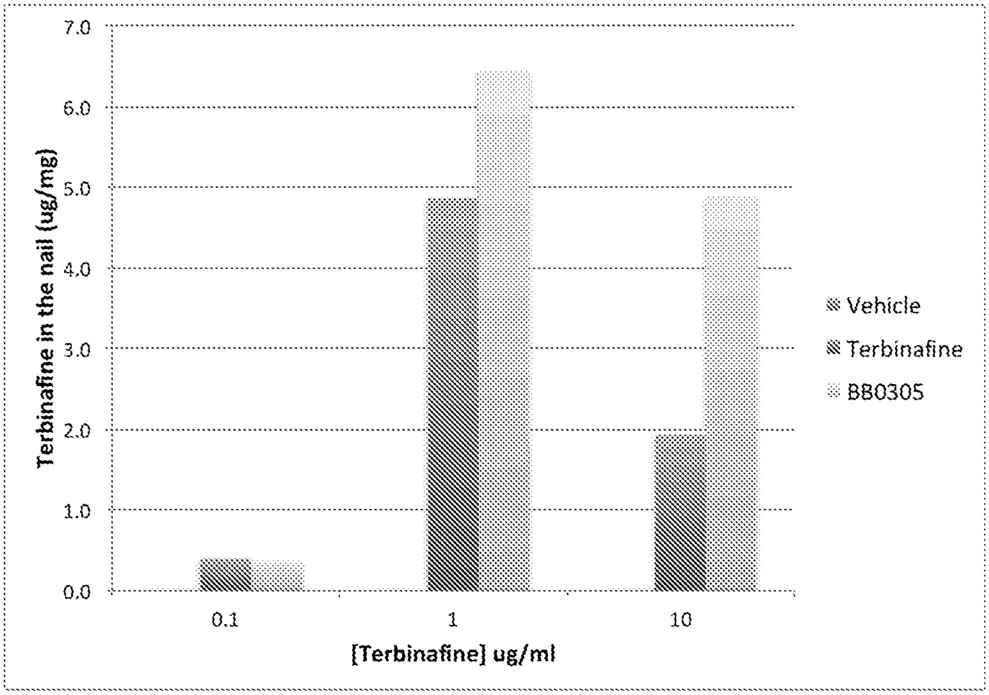
Figure 6B:
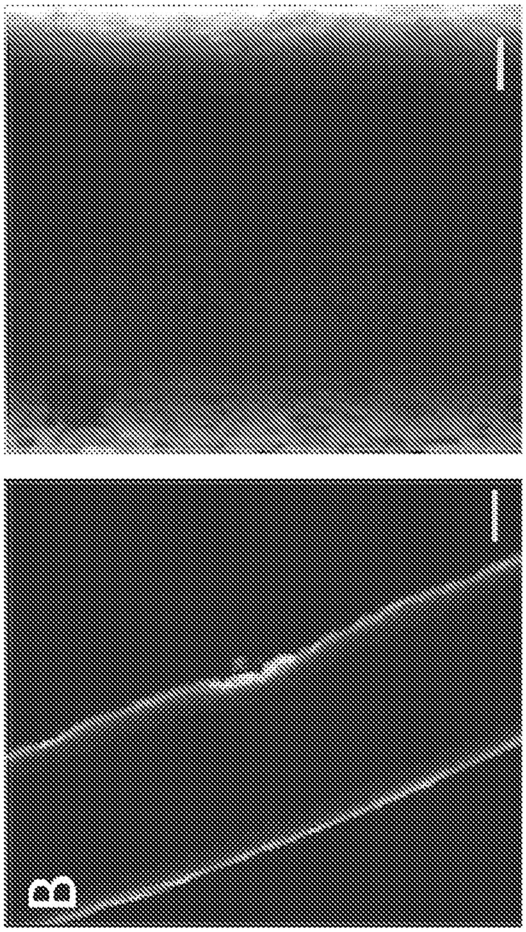
Figure 6A:
Figure 7:
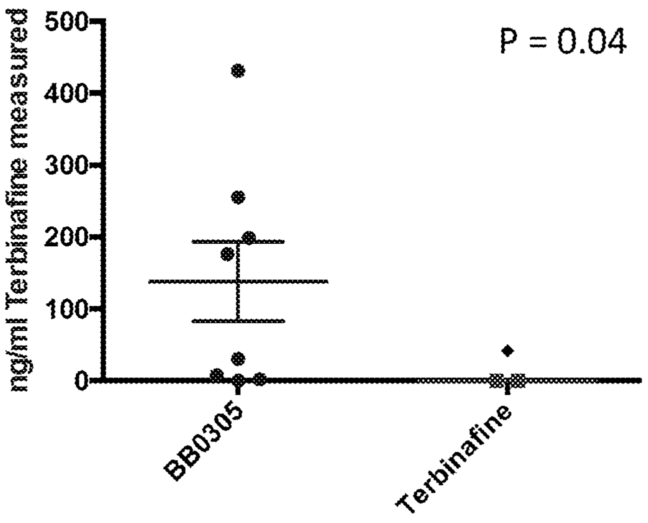
Figure 8:
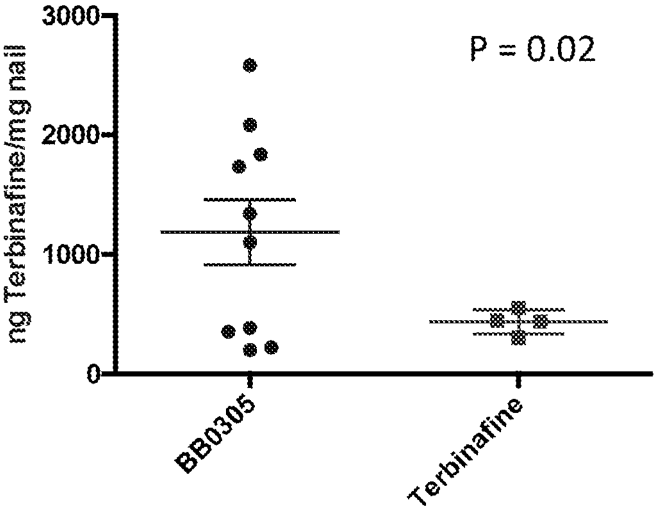
Figure 11A:
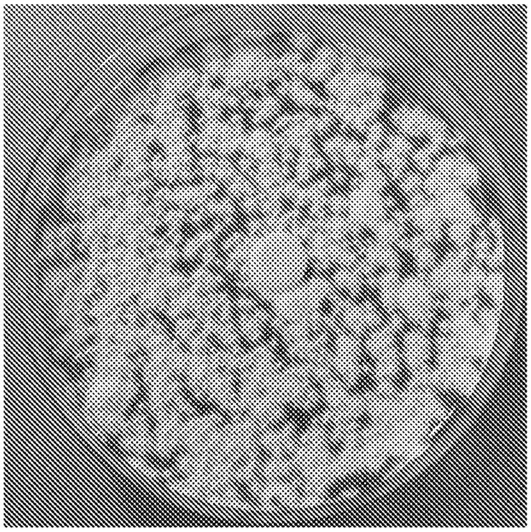
Figure 11B:
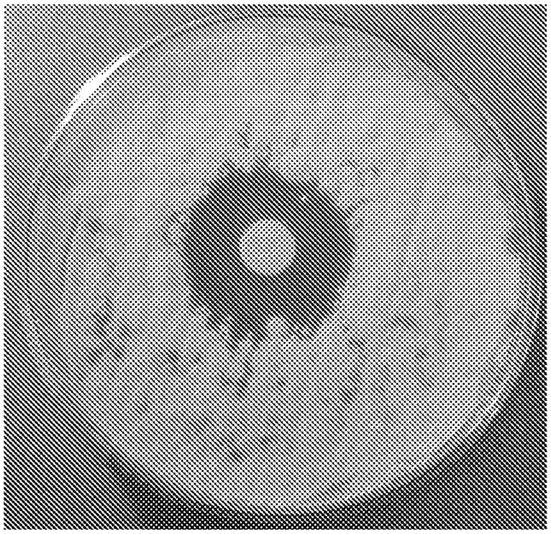
Figure 12:
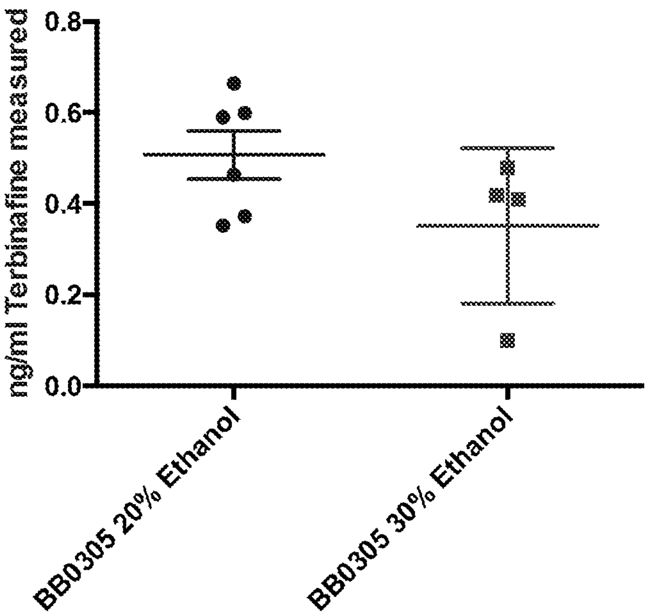
Figure 13:
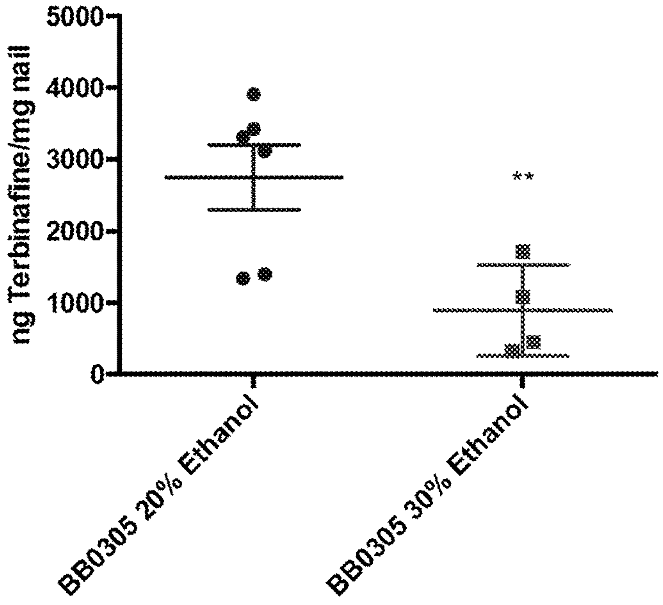
Figure 14:
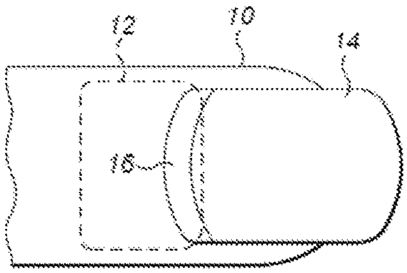
Figure 15:
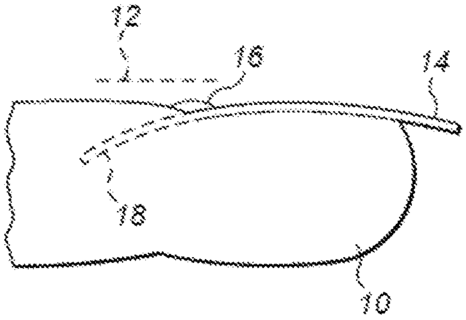
Figure 16:
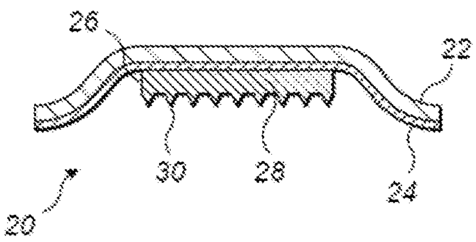

FIG. 2A is a histogram showing the size distribution of particles formed by mixing 0.1 mg/ml terbinafine and 0.3 mg/ml PHMB in 30% ethanol and incubating at room temperature for at least 24 hours. The particle size distribution was measured using Malvern Instruments Nanosight LM10 (particle size range=100-300 nm, mode size=195 nm, particle number=$12\times10^8$ particles/ml);

FIG. 2B is a video frame image of particles formed by mixing 0.1 mg/ml terbinafine and 0.3 mg/ml PHMB in 30% ethanol and incubating at room temperature for at least 24 hours. The particles were visualised using Malvern Instruments Nanosight LM10;

FIG. 3 is a graph showing the size distribution by intensity of the nanoparticles formed of 0.3 mg/ml PHMB/0.1 mg/ml terbinafine nanoparticles measured on a Malvern instruments Zetasizer;

FIG. 4A is a graph showing the number of terbinafine and PHMB nanoparticles per ml over time, where the stability of the nanoparticles was assessed for 170 days and a solution of BB0305 in 30% (v/v) ethanol at an equivalent concentration of 0.1 mg/ml terbinafine was stored in a clear plastic screw cap tube under ambient conditions of temperature and light. On the indicated days a sample was removed and analysed for the total number of nanoparticles/ml;

FIG. 4B is a graph showing the modal particle size of terbinafine and PHMB nanoparticles over time, where the stability of the nanoparticles was assessed for 170 days and a solution of BB0305 in 30% (v/v) ethanol at an equivalent concentration of 0.1 mg/ml terbinafine was stored in a clear plastic screw cap tube under ambient conditions of temperature and light. On the indicated days a sample was removed and analysed for the total number of nanoparticles/ml;

FIG. 5 is a graph showing the results of the nail soak experiments with BB0305 (terbinafine and PHMB nanoparticles) and terbinafine alone where 3 mm human nail discs from healthy nail clippings were suspended in BB0305 and terbinafine solutions at equivalent concentrations of active ingredient (0.1, 1 and 10 mg/ml). Washed, dried nails were dissolved in 5M NaOH and the levels of terbinafine determined by quantitative LC-MS/MS;

FIG. 6A is a photograph of a cryosectioned histological sample of a nail clipping from a healthy human volunteer which was soaked for 24 hours at 32° C. in a solution of 0.25 mg/ml PHMB, 0.05 mg/ml FITC labelled PHMB (1 in 5 spike of fluorescently labelled PHMB) and 0.1 mg/ml terbinafine (scale bar is approximately 100 μm);

FIG. 6B is a photograph of a cryosectioned histological sample of a nail clipping from a healthy human volunteer which was soaked in a similar manner to FIG. 6A. Two images are presented of the whole nail section (left hand side scale bar is approximately 100 μm) and the central region of the nail alone (right hand side scale bar is approximately 20 μm). Staining is clearly seen around the margin of the nail that penetrates at least 20 μm into the nail structure itself;

FIG. 7 is a scatter plot graph showing the penetration of terbinafine through healthy human nail samples treated with BB0305 (terbinafine and PHMB nanoparticles) or terbinafine solutions. The concentration of terbinafine was determined by LC-MS/MS in ethanol washes from healthy human nails treated with BB0305 or 0.1 mg/ml terbinafine solutions. Individual samples are plotted. (Diamond shape marker) All terbinafine samples (n=4) were below the limit of detection (<0.1 ng/ml). The two sample sets were compared using a student's unpaired parametric T-test by assuming that the concentrations of terbinafine passing through the nails treated with terbinafine solutions was 0.1 ng/ml (the limit of LC-MS/MS detection). The p-value for this test was 0.04;

FIG. 8 is a scatter plot graph showing levels of terbinafine associated with nails treated with BB0305 (terbinafine and PHMB nanoparticles) or terbinafine solutions. The concentration of terbinafine was determined by LC-MS in dissolved nails samples from healthy human nails treated with BB0305 or 0.1 mg/ml terbinafine solutions. Individual samples are plotted. The two sample sets were compared using a student's unpaired parametric T-test. The p-value for this test was 0.02;

FIG. 9A is a scatter plot graph showing a summary of Franz cell data from multiple dose addition of BB0305 (terbinafine and PHMB nanoparticles) to human nail where the concentration of terbinafine (determined by LC-MS/MS) in ethanol washes from healthy human nails treated with multiple small doses of BB0305 was investigated;

FIG. 9B is a scatter plot graph showing a summary of Franz cell data from multiple dose addition of BB0305 (terbinafine and PHMB nanoparticles) to human nail where the concentration of terbinafine (determined by LC-MS/MS) in dissolved nail samples from healthy human nails treated with multiple small doses of BB0305 was investigated;

FIGS. 10A-10E are photographic images of yeast extract peptone dextrose (YEPD) agar plates with *Trychophyton mentagrophytes* after incubation for 4 days at 30° C. Each plate had a 10 mm sterile paper disc placed in the centre of the *T. mentagrophytes* lawn. 40 µl of double distilled water or terbinafine solution of varying concentration was spotted onto each paper disc. The concentration of the terbinafine solutions used were: 0 µg/ml (control, FIG. 7A), 0.06 µg/ml (FIG. 7B), 0.6 µg/ml (FIG. 7C), 6.00 µg/ml (FIG. 7D) and 60.0 µg/ml. FIG. 8 is a plan view diagram of a finger with a nail which is to be treated with a micro-needle patch for delivering the composition of the present invention;

FIGS. 11A and 11B are photographic images of YEPD plates assessing the efficacy of BB0305 (terbinafine and PHMB nanoparticles) and terbinafine samples passing through healthy human nail against *Trychophyton mentagrophytes* A lawn of *Trychophyton mentagrophytes* was spread onto YEPD agar plates supplemented with 50 µg/ml chloramphenicol. The aqueous samples from the Franz cell collection chamber following 7 days treatment of healthy human nails with either 0.1 mg/ml terbinafine (FIG. 11A) or BB0305 (FIG. 11B) were spotted onto 10 mm paper discs. The discs were placed in the middle of the *Trychophyton* plates, which were then incubated at 30° C. for 5 days to allow the fungi to grow. Antifungal activity of terbinafine from the BB0305 treated nails is seen as a zone of clearance around the disc;

FIG. 12 is a scatter plot graph showing terbinafine concentrations in ethanol washes from nails treated with multiple doses of BB0305 (terbinafine and PHMB nanoparticles). The concentration of terbinafine (determined by LC-MS/MS) in ethanol washes from healthy human nails treated with multiple small doses of BB0305 was either 20% (v/v) ethanol (left hand side) or 30% (v/v) ethanol (right hand side);

FIG. 13 is a scatter plot graph showing terbinafine concentrations in the dissolved nails from nails treated with multiple doses of BB0305 (terbinafine and PHMB nanoparticles). The concentration of terbinafine (determined by LC-MS/MS) in dissolved nails from healthy human nails treated with multiple small doses of BB0305 was either 20% (v/v) ethanol (left hand side) or 30% (v/v) ethanol (right hand side);

FIG. 14 is a plan view of a finger with a nail which is to be treated with a micro-needle patch for delivering the composition of the invention;

FIG. 15 is a cross-sectional diagram of a finger as shown in FIG. 14; and FIG. 16 is a cross-sectional diagram of a micro-needle patch.

The aim of the following experiments was to investigate whether cellular delivery of antifungals (in particular for the treatment of onychomycosis) could be enhanced using a nanotechnology based delivery system with a cationic polymer Polyhexamethylene Biguanide (PHMB). PHMB is an inexpensive, readily available disinfectant and antiseptic used commonly in dressings, swimming pools and contact lens solutions. It is believed that its antiseptic action works by disrupting cell membranes of organisms and thereby causing leakage of cell contents. The experiments also assessed the effects of different concentrations and formulations of an antifungal agent on fungal species to enable determination of suitable dosage levels and formulations.

Nanoparticle Formation with Terbinafine and PHMB

Experiments were initially conducted to form nanoparticles of terbinafine and PHMB. These terbinafine and PHMB nanoparticles were denoted BB0305 throughout the experiments.

BB0305 nanoparticles were initially formed through the combination of terbinafine·HCl with PHMB in 30% (v/v) ethanol to final terbinafine concentrations equivalent to 0.1 mg/ml, 1 mg/ml or 10 mg/ml. Nanoparticle formation was routinely confirmed on a Nanosight LM10 instrument (Malvern Instruments). Additional nanoparticle analyses were carried out using a Zetasizer (Malvern Instruments). Control terbinafine solutions were made by dissolving terbinafine·HCL in 30% (v/v) ethanol to final concentrations of 0.1 mg/ml, 1 mg/ml or 10 mg/ml.

Initial formulations of terbinafine with PHMB in 30% ethanol were shown to significantly increased the number of nanoparticles formed and resulted in the formation of more mono-disperse nanoparticles than the particles formed with terbinafine alone in 30% ethanol. The results showed that PHMB could be used to form mono-disperse nanoparticles with an antifungal agent which could then be used in the preparation of a topical medicament for the subsequent treatment of a range of potential fungal infections.

Analysis of Nanoparticles

Solutions of BB0305 showed clear formation of nanoparticles that were stable at room temperature for over 5 months.

Figure 1A:
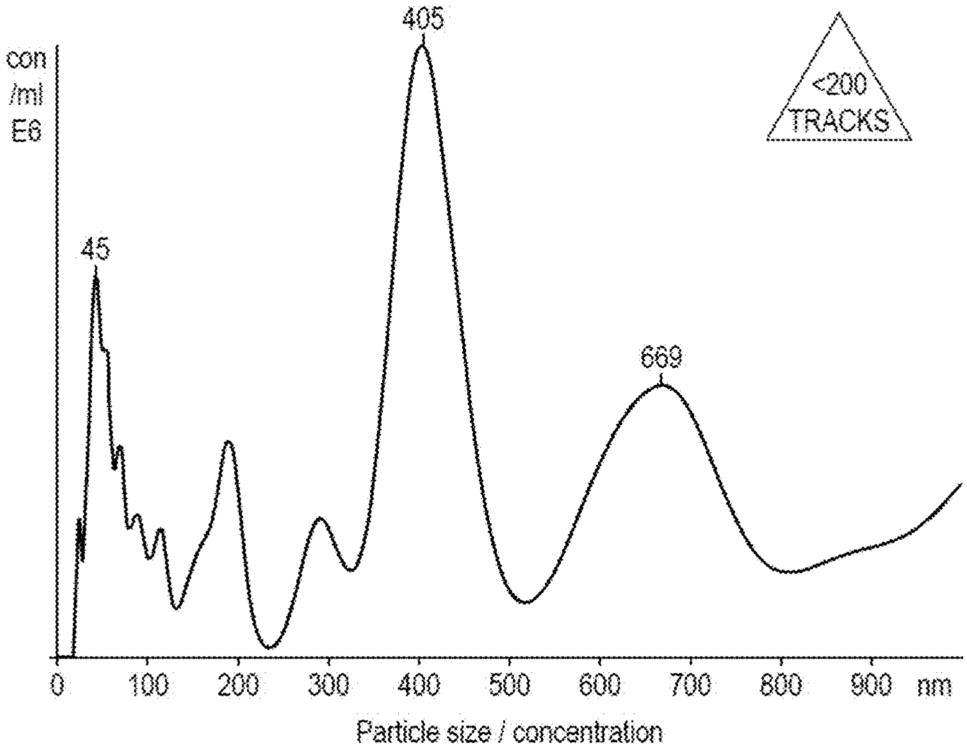
FIG. 1A is a histogram showing the size distribution of particles formed by mixing 0.1 mg/ml terbinafine in 30% ethanol and incubating at room temperature for at least 24 hours. The particle size distribution was measured using Malvern Instruments Nanosight LM10 (particle size range=50-800 nm, particle number=$0.5\times10^8$ particles/ml)

Initial analysis used a Nanosight LM10 nanosizer (Malvern Instruments) to detect nanoparticles in solution. Terbinafine solutions contained detectable particles in this analysis (as shown in FIG. 1A). However the number of particles/ml of solution was relatively low ($<0.5\times10^8$/ml for a solution of 0.1 mg/ml terbinafine in 30% (v/v) ethanol) and the particle sizes were heterogeneous and polydispersed. The presence of these particles were thought to at least in part be due to the hydrophobic nature of the compound meaning that it is not fully solubilized and hence contains a range of drug aggregates in aqueous solution.

Figure 1B:
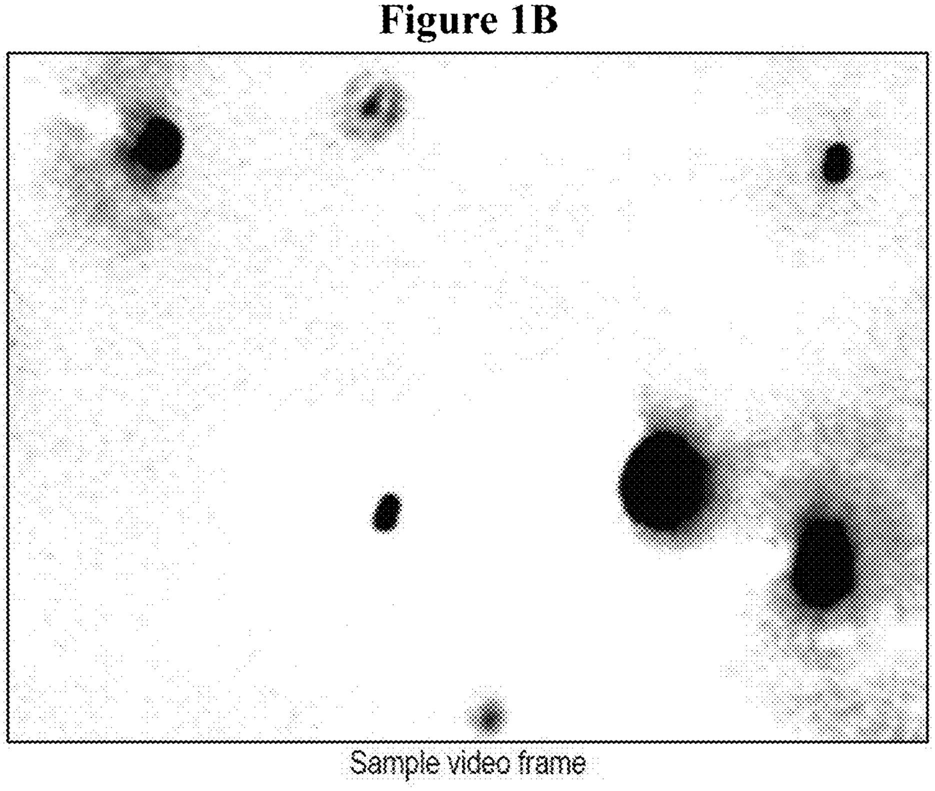
FIG. 1B is a video frame image of particles formed by mixing 0.1 mg/ml terbinafine in 30% ethanol and incubating at room temperature for at least 24 hours. The particles were visualised using Malvern Instruments Nanosight LM10.

In contrast, in a solution of BB0305 at an equivalent concentration of 0.1 mg/ml terbinafine, a large number (typically between $5\text{-}10\times10^8$ nanoparticles/ml) of monodispersed particles with diameters in the range of 170-210 nm (as shown in FIG. 1B) were observed. Higher concentrations of BB0305 (equivalent concentrations of terbinafine of 1 and 10 mg/ml respectively) were also produced for use in initial nail soak experiments (as described below) but these showed a loss of monodispersity, thought to be due to the higher polymer concentration allowing the formation of larger nanoparticle aggregates (data not shown).

The LM10 uses direct visualisation of the particles through a microscope where particles are tracked by a video camera and their sizes calculated using the Einstein-Stokes equation, which relates particle velocity in a solution to their diameter. This video capture also allows for a qualitative assessment of different formulations during their analysis. However, this instrument has a lower cut-off range of approximately 20 nm diameter for analysis. Nanoparticles were therefore also analysed BB0305 on a Zetasizer (Malvern Instruments), which used dynamic light scattering to calculate particle size and is able to detect particles with sizes down to 0.3 nm. This analysis (as shown in FIG. 3) identified a second population of nanoparticles in BB0305 with diameters in the range of 0.3-2 nm, which could not be detected by the LM10.

Finally the long-term stability of a solution of BB0305 in 30% (v/v) ethanol was assessed by measuring the nanoparticles in solution over a period of 170 days (as shown in FIGS. 4A and 4B). Analysis was performed using a Nanosight LM10 and so only considered the larger diameter population of BB0305 nanoparticles. This analysis demonstrated that, despite an initial modest reduction in the number of particles in solution and some variation in the modal size of the particles, BB0305 nanoparticles were essentially stable for at least 5 months at room temperature under ambient light conditions.

Nail Soak Experiments

Samples of healthy human nail were pre-incubated at 30° C. in $ddH_2O$ for 2 hours. 3 mm discs were then cut from the clippings using a 3 mm biopsy punch. The nail discs were placed in 250 μl of test solutions in a 1.5 ml tube and incubated at 24 hours at 32° C. in a humidified incubator at 0.5% (v/v) $CO_2$ Nail samples were removed and washed in a large volume of $ddH_2O$ to remove any drug solution on the nail. The nails were dried using a clean tissue and then weighed. The weighed nails were dissolved in 200 μl of 5M NaOH at 37° C. for 1 hour. After being dissolved, 200 μl of methanol was added to the samples to ensure that any terbinafine in the samples remained in solution. The amount of terbinafine in dissolved nail sample solutions were analysed using quantitative LC-MS/MS mass spectrometry.

Quantitative mass spectrometry (MS) was used to detect and quantify terbinafine in samples. Sample identifiers were blinded prior to submission for analysis. Analyses used high performance liquid chromatography with tandem mass spectrometry (LC-MS/MS) using a Waters Acquity I-Class UPLC chromatography system coupled with a Waters Xevo TQ-S Mass Spectrometer. Levels of terbinafine were quantified against drug standards on a standard curve from 0.1-10 ng/ml terbinafine. Samples were appropriately diluted to ensure they fell within the standard curve. Samples below 0.1 ng/ml terbinafine were below the limit of detection for this analysis. Concentrations of terbinafine in the nail samples were normalised to the total amount of nail and expressed as ng terbinafine/mg of nail.

Initial research focused on using simple nail "soak" experiments in which 3 mm discs of human nail were incubated in different formulations and test solutions. These experiments were only able to detect whether terbinafine was associating with nail and did not give direct evidence of nail penetration. However they were technically simple to perform, relatively high-throughput and enabled a range of different formulations to be assessed.

As shown in FIG. 5, terbinafine in simple solutions of terbinafine associate with human nail samples. The amount of terbinafine associated with the nail was concentration dependent between 0.1 mg and 1 mg/ml but did not show any further enhancement at a higher concentration of 10 mg/ml. This would indicate that above 1 mg/ml the nail disc has reached an upper limit for the amount of terbinafine that can associate with it.

FIG. 5 also illustrates that BB0305 associates with human nail samples. At an equivalent concentration to 0.1 mg/ml terbinafine no significant difference between BB0305 and a solution of terbinafine was seen, and both produced equivalent concentrations of drug in the dissolved nail samples. As had been observed for terbinafine, there was also an increase in drug association between BB0305 at terbinafine concentrations equivalent to 0.1 and 1 mg/ml but no further increase at 10 mg/ml. Again suggesting that above 1 mg/ml, BB0305 had reached the limit of the amount of drug that can soak into the nail disc in 24 hours. However, compared to terbinafine treated nails, the maximum amount of drug that can associate with nails treated with BB0305 was much higher (1.3-2.5×). This increase was not due to differences in the accessible nail surface or overall nail material as all the test were performed on 3 mm nail discs with essentially the same surface area and had weights that only varied by <10% between samples. These experiments therefore suggested that BB0305 increases the maximum amount of terbinafine that can associate with human nail, which indicated that the formulation is enhancing drug delivery into the tissue.

Although the nail soak experiments suggested that BB0305 enhanced drug delivery into nails, they were unable to distinguish between increased drug penetration into the nail and increased drug binding to the nail. It was therefore decided to advance the 0.1 mg/ml BB0305 formulation into histology studies in order to try and obtain direct evidence of nanoparticle penetration into the tissue. This concentration was chosen because it produced the most robust and consistent nanoparticle formulation and, as discussed previously, higher concentrations of BB0305 were much more variable in forming nanoparticles.

Histology Studies

Formulations of BB0305 were made at an equivalent concentration of 0.1 mg/ml terbinafine that included a 1% (w/w) "spike" of FITC conjugated Nanocin™ (a nanoparticle based delivery platform, consisting of PHMB, marketed by Tecrea Ltd, The London Bioscience Innovation Center, 2 Royal College Street, London, NW1 ONH, UK). The labelled BB0305 was used in a nail soak experiment as described above. The washed and dried nails were then sent for histology analyses. Histology and fluorescence microscopy was carried out on frozen cryosections of nail.

Example images from histology studies with FITC labelled BB0305 are shown in FIGS. 6A and 6B. Strong fluorescence was observed around the margins of the nails, consistent with BB0305 binding to the surface of the nail. In addition, we also observed staining penetrating into the nail from the surface. The level of staining varied but we were able to detect fluorescence deep within the nail structure itself (as shown in FIG. 6A in particular).

Although this data is highly suggestive that BB0305 nanoparticles are penetrating into human nail the possibility that the staining observed was only due to free FITC-Nanocin™ needed to be eliminated. It was therefore decided to progress from these histology experiments to using Franz cells and directly measure drug transit across human nail samples.

Franz Cells Nail Penetration Studies

Nail clippings were soaked in water overnight at 30° C. and dried briefly. A 3 mm diameter punch was used to take disc biopsies of the nail clippings. Each nail disc was added to a Franz cell and an upper chamber of the cell attached. 40 µl of the following formulations was added to the upper chambers: 0.3 mg/ml PHMB+0.1 mg/ml terbinafine; or 10 mg/ml terbinafine. Lower collection chambers of the Franz cells were filled with water (approximately 600 µl) and the hole in the base of the sample chamber also filled with $ddH_2O$ to prevent bubbles forming beneath the nail. The upper sample chamber was carefully placed into the collection chamber ensuring not to introduce any air bubbles. Excess liquid from the collection chamber was expelled at this point leaving a final volume of liquid in the lower chamber of 500 µl. Parafilm® was used to wrap the join between the upper and lower chambers to prevent liquid evaporation.

For single dose (continuous exposure) experiments, 40 µl of the relevant test sample (BB0305 or terbinafine control) was added into the upper sample chamber using a fine pipette tip, ensuring not to introduce any air bubbles at the nail/liquid interface. The upper chamber was sealed to limit evaporation. For the multiple dose experiments, 5 µl of sample was added every day for 7 days into the upper sample chamber directly onto the nail using a fine pipette tip, ensuring that no air bubbles were introduced at the nail/liquid interface. The chamber was left open to allow the sample to evaporate. Franz cells were incubated at 32° C. in a humidified incubator at 0.5% (v/v) $CO_2$.

Following incubation of the Franz cell, the sample chamber and collar assembly were carefully removed and all of the liquid taken from the lower collection chamber and hole in the base of the collar. The sample chamber and collar assembly was inverted and the undersides of the nails were then gently washed with 5×20 µl of ethanol to remove any drug associated with the underside of the nail. The combined ethanol washes were retained for analysis (100 µl total volume). This wash was intended to capture any terbinafine that might have passed through the nail. Terbinafine found in either the lower collection chamber or ethanol washes of the underside of the nails represented drug that had passed through the nail.

The nail discs from the Franz cell were also analysed for the presence of terbinafine as follows: the remaining test sample was removed from the upper sample chamber and discarded and the sample chamber washed 5 times with 100 µl $ddH_2O$, with each wash being discarded, in order to remove any residual test solution remaining in the sample chamber.

The sample chamber and collar were then disassembled and the nail samples removed. The nails were washed by immersion in a large volume of $ddH_2O$, dried using a clean tissue and weighed. The weighed nails were then dissolved in 200 µl of 5M NaOH at 37° C. for 1 hour. After being dissolved, 200 µl of methanol was added to the samples to ensure that any terbinafine in the samples remained in solution.

FIGS. 7-9B summarise the data from Franz cell analyses of drug transit across human nails samples. Only the data present from the dissolved nail samples and ethanol washes of the underside of the nail are provided as these observations proved to be the most robust between samples. However, it was always possible to detected terbinafine in the lower chamber of nails treated with BB0305, sometimes to very high levels (>0.6 µg/ml). It is believed that this analysis represents a conservative view of the amount of terbinafine passing through the nail in BB0305 treated samples.

Single Dose (Constant Exposure) Experiments

40 µl of solutions of BB0305 (equivalent to 0.1 mg/ml terbinafine) or terbinafine (0.1 mg/ml) in 30% (v/v) ethanol were added to the sample chamber of Franz cells containing healthy human nail samples. The cells were then incubated at 32° C. for 7 days. The samples remained in contact with the upper nail surface for the duration of each experiment. After 7 days, samples from the underside of the nail (ethanol washes) were collected and analysed by LC-MS/MS. Nail samples on day 7 were washed and dissolved using 5M NaOH as described earlier. All the samples collected were analysed for the presence of terbinafine using high performance liquid chromatography with tandem mass spectrometry (LC-MS/MS) on a Waters Acquity I-Class UPLC chromatography system coupled with a Waters Xevo TQ-S Mass Spectrometer. Levels of terbinafine were quantified against drug standards. The limit of detection in these analyses was 0.1 ng/ml.

As shown in FIGS. 7 and 8, samples treated with BB0305 consistently demonstrated penetration of terbinafine through healthy human nail samples. Terbinafine could be detected both in the collection chamber solution and ethanol washes of the underside of the nail as early as 1 day of incubation. Analysis of the ethanol washes from the underside of nails treated with BB0305 for 7 days demonstrated robust drug delivery by BB0305 through the nail (as shown in FIG. 7). The amount of delivery varied between samples, probably due to natural variation in the nail samples, but in all cases would be predicted to be greater than that required to achieve a mycological killing dose.

In contrast, terbinafine solutions did not penetrate the nail and in all the experiments using an equivalent drug concentration to BB0305 (0.1 mg/ml) the amount of terbinafine passing through the nail was below the limit of detection (<0.1 ng/ml) in the LC-MS/MS (as illustrated in FIG. 7). By assuming that terbinafine had penetrated to a concentration of 0.1 ng/ml a statistical test could be applied to the data to demonstrate that the BB0305 results are significantly different to those of simple terbinafine solutions. The p value of 0.04 calculated in this analysis is an underestimate of significance because the highest possible concentration of terbinafine in the simple terbinafine treated samples was assumed.

The amount of terbinafine in the dissolved nail samples from the Franz cell was also determined at day 7 (as shown in FIG. 8). This represented the amount of drug bound to the top face of the nail (which was not washed off prior to dissolution with 5M NaOH) together with any drug within the nail itself i.e. drug penetrating the nail but not reaching the other side. Similar to our nail soak experiments (FIG. 5), we saw significantly higher amounts of terbinafine associated with the nails treated with BB0305 compared to terbinafine alone (median difference of approximately 2 fold, p=0.02). This is again consistent with the belief that BB0305 enhances delivery of terbinafine into (and through) the nail.

Multiple Dose Experiments

In the single dose experiments the test solution remains in constant contact with the upper surface of the nail during the entire period of incubation. This does not necessarily reflect the reality of patient application in which the drug would be applied daily to an infected nail and then allowed to dry. Therefore to try and replicate this situation experiments were performed in which 5 µl of BB0305 was added daily to the nail in the Franz cells. This small volume was sufficient to cover the nail discs surface but evaporated prior to the next addition, mimicking more closely a patient applying BB0305 as a daily topical treatment. Samples from the ethanol washes of the nail underside and nail itself were collected and analysed by LC-MS/MS for the presence of terbinafine as described earlier.

In the multiple dose experiments substantial amounts of terbinafine was detected associated with the nails themselves (as illustrated in FIGS. 9A and 9B). This was at a level that was not too dissimilar to that observed in the single dose (constant exposure) experiments with BB0305 (as shown in FIG. 8) and was again higher than the terbinafine controls from the single dose experiment. Significant amounts of terbinafine in the ethanol washes from the undersides of the nail was also detected indicating that the drug had also passed through the nail in this experiment. Compared to the single dose (constant exposure) experiments the levels of drug delivered through the nail were much lower in the multiple dosing experiments. This is consistent with the belief that longer treatment with BB0305, the greater delivery of terbinafine through the nail.

*Trychophyton Mentagrophytes* Anti-Fungal Assay

Earlier experiments had clearly shown that BB0305 delivers terbinafine through the nail but it had to be established that the passage of the drug through the nail would not cause chemical modification leading to a loss of efficacy. An anti-fungal assay using lawns of *T. mentagrophytes* was therefore performed.

*T. mentagrophytes* is a laboratory fungal species relevant to the major pathogens associated with onychomycosis (see for example Wade Foster et al, *J. American Acad. Dermatology.* 2004. 50(5). pp 748-752) and so efficacy against this species would be expected to translate to efficacy against pathogenic *Trychophyton* species such as *T. rubum* (Table 1 below).

TABLE 1

In vitro activity of terbinafine (taken from Leyden, *J. Am. Acad. Dermatol.* 1998. 38: S42-7).

| Fungus | No. strains tested | MIC range (μg/ml) |
|---|---|---|
| *Epidermophyton floccosum* | 42 | 0.001-0.047 |
| *Microsporum* species | 25 | 0.002-0.07 |
| *Microsporum canis* | 49 | 0.006-0.08 |
| *Trichophyton* species | 27 | ≤0.06 |
| *Trichophyton rubrum* | 72 | 0.001-0.038 |
| *Trichophyton verrucosum* | 17 | 0.001-0.006 |
| *Trichophyton mentagrophytes* | 32 | 0.001-0.006 |
| *Trichophyton interdigitale* | 11 | 0.002-0.028 |
| *Trichophyton terestre* | 1 | 0.002 |

A single colony of *T. mentagrophytes* was picked from a stock plate and grown for 48 hours in 5 mls of YEPD (yeast extract, peptone, dextrose) medium at 30° C. A sterile swab was dipped into the resulting culture and then used to spread a lawn of *T. mentagrophytes* onto a YEPD agar plate supplemented with chloramphenicol (50 ug/ml). Chloramphenicol was included as samples from the Franz cell were not sterile and showed bacterial outgrowth on normal YEPD plates. A 10 mm sterile paper disc was soaked in test solution, the excess liquid removed and the disc placed onto the *T. mentagrophytes* lawn. Plates were inverted and incubated at 30° C. for 5 days.

The first experiment performed was to establish the approximate MIC (minimum inhibitor concentration) for terbinafine against *T. mentagrophytes* in a paper disc assay. To do this a 1:10 dilution series of terbinafine·HCl in $ddH_2O$ was generated from 60 μg/ml to 0.06 μg/ml. 10 mm sterile paper discs were then soaked in the various dilutions and these placed onto lawns of *T. mentagrophytes*. After 5 days of incubation, zones of clearance were observed around the discs with concentrations of terbinafine having anti-fungal activity against this species (as shown in FIG. 10). The MIC for terbinafine in this assay was 0.6 μg/ml and below this concentration no clear zone of clearance was observed. It was noted that the MIC in this assay is >100× higher than previously reported (6 ng/ml) for terbinafine against *T. mentagrophytes* (with reference to Table 1 above). The reported figures were certainly derived from a liquid MIC assay, which is known to be more sensitive, and so this paper disc assay represented a substantially more stringent test of drug efficacy.

This assay was also used to address the question of whether terbinafine passing through the nail in BB0305 treated samples still retained its antifungal efficacy. To do this a *T. mentagrophytes* lawn assay was performed using a sample of the aqueous phase from one of the Franz cell experiments that quantitative LC-MS/MS analysis demonstrated contained >0.6 μg/ml terbinafine (FIG. 11A-11B). Consistent with the MIC experiment and the quantitative MS results for this sample, a clear zone of clearance with BB0305 could be seen but no effect with the terbinafine control sample. Hence, terbinafine passing through a healthy human nail treated with BB0305 retained its efficacy and was still able to kill *T. mentagrophytes.*

Potential Efficacy of BB0305 in Onychomycosis

The aim with BB0305 was to match the performance of oral terbinafine with a topical formulation of the drug that would not have the safety issues associated with systemic drug exposure. Compared to terbinafine solutions, BB0305 was shown to significantly enhance the delivery of drug through healthy human nail. The key question is whether the amounts achieved by BB0305 dosing would be predicted to be efficacious in the treatment of onychomycosis. To address this question the concentrations of terbinafine observed in the Franz cell experiments were compared to those reported in the nails of patients treated with oral terbinafine (Leyden, *J. Am. Acad. Dermatol.* 1998. 38: S42-7).

Following oral dosing, terbinafine reaches a concentration of 0.1 μg/g in nails after 7 days treatment rising to about 0.25 μg/g after 3 weeks and 0.55 μg/g after 18 months (Leyden, 1998). All of these levels are higher than the MICs of a range of key fungal species associated with onychomycosis (Table 1) and hence explain the drugs efficacy in treating fungal nail infection in these patients.

BB0305 appears to vastly exceed this level in the dissolved nails (FIGS. 8 and 9A-9B), achieving median concentrations equivalent to approximately 1 mg/g of drug in the nail after 7 days (10000 fold higher than oral dosing). However, although lower, terbinafine alone also showed significant levels of drug associated with the dissolved nails (median concentrations of approximately 0.5 mg/g) yet trials with topical terbinafine (at much higher doses than used in these experiments) failed to show efficacy in the treatment of onychomycosis (Elewski et al., *Journal of the European Academy of Dermatology and Venereology.* 2013, 27(3), pp 287-294).

Although substantial amounts of drug are found associated with nails treated with terbinafine solutions, no significant amount of terbinafine was measured to pass through the nail in any of our samples (FIG. 7). So for these samples we concluded that the vast majority of the drug is bound to the upper surface of nail or not penetrating very far into the tissue.

In contrast to terbinafine treated samples, terbinafine was constantly detected on the underside of the nails treated with BB0305 indicating that the drug must have passed into and through the nail. Thus the measurement of terbinafine in the dissolved nails from BB0305 treated samples represents not just drug associated with the upper surface but also drug present throughout the entire depth of the tissue.

It is highly likely that in BB0305 treated nails, an asymmetric distribution of the drug is established, with a larger concentration at the upper (treated) surface and the lowest concentration of drug found towards the bottom of the nail. Because of this, the concentration of terbinafine in the lower portions of the nail was estimated, as this would be the lowest concentration of drug in our samples. To do this it was assumed that the level of drug found on the underside of the nail (in the ethanol washes) was equivalent to the concentration in the nail just above it in the nail disc. Although 3 mm diameter discs of nail were used in the Franz cell experiments, only a 1.5 mm diameter circle of nail is in contact with the solutions in the upper and lower chambers (the rest of the nail forms the seal with the chamber itself). This means that the terbinafine in the ethanol washes of the bottom of the nail is from a surface area of approximately 1.8 $mm^2$ of nail. In order to calculate an approximate concentration in the lower portion of the nail, it was assumed that this portion of the nail to have a depth of 0.1 mm. Overall the nails were about 0.5 mm thick and so this represents about a fifth of the overall nail disc. Thus the volume of the lower portion of the nail disc is 0.18 $mm^3$, equivalent to 0.18 µl. To calculate the concentration in of terbinafine in the lower portion of the nail it was assumed that this volume of nail contained an equivalent amount of terbinafine to that found in the ethanol washes.

The median concentration of terbinafine found on the underside of nails in the multi-dosing experiment was 0.4 ng/ml (FIG. 9A-9B), which is equivalent to 0.04 ng of total terbinafine in the samples. From this, it was estimated that the concentration of terbinafine in the lowest portion of the nail is therefore 220 ng/ml (0.04 ng/0.18 µl). Finally, the density of healthy human nail is 1.34 g/ml (Baraldi et al. 2015, *Pharm. Res.* 32(5), 1626-33) and so the concentration of terbinafine in the lowest portion of the nail is approximately equivalent to 0.165 µg/g (0.22 µg/ml/1.34 g/ml).

From this calculation it can be seen that the multi-dose experiments BB0305 delivered an amount of terbinafine into the lowest portions of the nail that is greater than the concentration of terbinafine reached by oral dosing after 7 days (0.165 µg/g compared to 0.1 µg/g). This level of drug is 2-3 fold higher than that required to kill the least sensitivity fungal species associated with onychomycosis (>0.06 µg/ml, see Table 1). For portions of the nail closer to the treatment surface we would expect the concentration to be much higher. These figures are based on the most conservative data from the multi-dose experiments. For the single dose experiments the median concentration of terbinafine found in the ethanol washes was 185 ng/ml (FIG. 7) and the equivalent predicted nail concentration of drug in the lower portions would be 8 µg/ml, vastly exceeding that achieved by oral dosing and needed for antifungal efficacy.

In summary, 7 days topical application of BB0305 promotes much greater association of terbinafine with healthy human nail than simple terbinafine solutions. Furthermore, BB0305 enables terbinafine to penetrate all the way through the nail indicating that this increase in drug nail levels is due, at least in part, to enhanced drug penetration into the tissue. Even portions of the nail most distal from BB0305 applications are predicted to achieve concentrations of drug that exceed those produced by equivalent oral dosing. This level is greater than the MICs of relevant fungal species and therefore likely to be efficacious in the treatment of onychomycosis.

Oral terbinafine is currently the 'gold standard' for the treatment of onychomycosis and has the highest cure rates with the shortest treatment times (>80% cure following 3-6 months of dosing). However, its use in the treatment of the disease is limited by its safety profile and the fact that terbinafine has significant drug-drug interactions. A large number of these issues are almost certainly due to oral dosing (e.g. liver toxicology, CNS effects) and subsequent high systemic drug exposure. Other topical onychomycosis treatments require long treatment regimes (up to 18 months treatment), have low cure rates (20-40%) and show high rates (>50%) of disease recurrence (Ha/my, K. *J. Am. Acad. Dermatol,* 2005. 52(3): 126-126, Scher et al. *J Am Ac Dermatol.* 2007; 56(6):939-944). Producing an effective topical formulation of terbinafine is a highly attractive approach to the treatment of onychomycosis because it takes the drug with the best-proven clinical efficacy and removes the safety issues associated with systemic exposure. Achieving this has proven to be challenging and many previous trials with a topical terbinafine solution failed to demonstrate any significant efficacy in the treatment of onychomycosis.

As described above, the amount of terbinafine present in BB0305 for topical application is much lower than would be required for current oral doses. Current systemic treatments would typically employ a daily 250 mg dose of oral terbinafine over 7 days. After 7 days of daily topical application of small volumes of BB0305 to nail samples (mimicking daily patient applications) higher levels of terbinafine in the nail were achieved than reported for oral doses. The drug levels found in the nails are much higher than would be required to show efficacy against all relevant fungal species associated with onychomycosis (Table 1). To give an idea of context, from these experiments the dose of BB0305 that would have been needed to treat an average nail (100 $mm^2$) would have been about 200 µg for a week compared to 1.75 g terbinafine for oral treatment i.e. an 8750 fold lower dose.

Finally, healthy human nails are a much more stringent test of drug penetration. A recent publication by Baraldi et al. (Baraldi et al. 2015), demonstrated that although nails are thicker in onychomycosis, they suffer a significant lose of integrity meaning they are much more permeable to aqueous solutions (3-4 times greater). As such we would expect BB0305 to show even better drug penetration properties in diseased tissue.

Comparison of BB0305 in 20% (v/v) Ethanol Vs. 30% (v/v) Ethanol

All the above experiments employing BB0305 were conducted in solutions of 30% (v/v) ethanol. Initial formulation studies had demonstrated that 30% (v/v) ethanol produced the highest number of BB0305 nanoparticles whilst experiments in solutions of 10% (v/v) ethanol or lower showed a substantial drop-off in particle numbers. Although 30% (v/v) ethanol is an acceptable solution for use in the treatment of topical fungal infections, different (v/v) ethanol was assessed to see whether lower ethanol content would still maintain efficacy. It was therefore decided to look at formulations of BB0305 in 20% (v/v) ethanol.

Formulations of BB0305 were made as described above, but using 20% (v/v) ethanol instead of 30% (v/v) ethanol. Analyses on the NanoSight LM10 showed no detectable differences in the 20% (v/v) formulations in either the particle numbers or particle distributions of BB0305 compared to 30% (v/v) ethanol. A number of multiple-dose Franz cell experiments with BB0305 formulations in 20% (v/v) ethanol was therefore performed as they best mimicked the type of daily topical dosing a patient would use and were therefore the most meaningful in modeling the efficacy of drug treatment in onychomycosis.

The amount of terbinafine found in the ethanol washes of the undersides of nails treated for a week with daily additions of 5 µl of BB0305 in 20% (v/v) ethanol was analyzed by LC-MS/MS as described in the main text (as illustrated in FIG. 12). These demonstrated a consistent level of terbinafine passing through the nails with a mean value of 0.5 ng/ml in the washes. The data showed a slightly higher trend in the amount of terbinafine passing through the nails treated with BB0305 in 20% (v/v) ethanol suggesting that BB0305 in 20% (v/v) was more effective at delivering drug through the nail. Consistent with this, the amount of terbinafine in the dissolved nails treated with BB0305 in 20% (v/v) ethanol was three-fold higher that those treated with BB0305 in 30% (v/v) ethanol (as shown in FIG. 13).

Taken together, these results demonstrated that using formulations of BB0305 in 20% (v/v) ethanol enhances further the delivery of terbinafine into and through the human nail in Franz cell multiple-dose (daily addition) experiments. Substantially higher amounts of drug are found associated with the nail and the amount of terbinafine passing through the nail is also higher. Calculations show that the median amount of drug in the lower portions of the nail treated with this formulation of BB0305 would be 0.21 µg/g, which is twice that achieved in nails following oral dosing at 7 days and well above that required to kill relevant fungal species in onychomycosis. This result is consistent with the observations of Baraldi et al. (Baraldi et al. 2015) that compounds in aqueous solution have higher levels of penetrance into both healthy and diseased nails compared to those in a 50% (v/v) ethanol solution.

In summary, reducing the ethanol concentration in solutions of BB0305 from 30% to 20% (v/v) has no detectable impact on nanoparticle formation, but interestingly, formulations of BB0305 in 20% (v/v) ethanol demonstrate improved terbinafine delivery properties both into and through healthy human nail in Franz cell experiments mimicking the daily application of drug in the treatment of onychomycosis.

Formulations of Onychomycosis Medicaments

It is envisaged that in-light of the above experiments, the following formulation would be effective as a topical medicament for onychomycosis:

Formula A

| Ingredient | Amount |
|---|---|
| Terbinafine•HCl | 100 µg/ml |
| PHMB | 300 µg/ml |
| Ethanol | 20% (v/v) |
| Distilled water | ≥80% (v/v) |

Other formulations may also provide effective topical medicaments:

Formula B

| Ingredient | Amount |
|---|---|
| Terbinafine•HCl | 100 µg/ml |
| PHMB | 300 µg/ml |
| Ethanol | 30% (v/v) |
| Distilled water | ≥70% (v/v) |

Formula C

| Ingredient | Amount |
|---|---|
| Terbinafine•HCl | 50 µg/ml |
| PHMB | 150 µg/ml |
| Ethanol | 20% (v/v) |
| Distilled water | ≥80% (v/v) |

Formula D

| Ingredient | Amount |
|---|---|
| Terbinafine•HCl | 200 µg/ml |
| PHMB | 600 µg/ml |
| Ethanol | 20% (v/v) |
| Distilled water | ≥80% (v/v) |

Formula E

| Ingredient | Amount |
|---|---|
| Terbinafine•HCl | 150 µg/ml |
| PHMB | 450 µg/ml |
| Ethanol | 30% (v/v) |
| Distilled water | ≥70% (v/v) |

It will of course be apparent to the skilled addressee that commonly used medicinal components may be used in conjunction with the above Formulas A to E, including: buffers, excipients, binders, oils, water, emulsifiers, glycerine, antioxidants, preservatives and fragrances, and urea. Such components may be used in part to replace the water content and enable the medicament to be formulated into suitable topical forms such as creams, ointments or sprays.

A formulation in accordance with the present invention was prepared according to Formula F below and denoted BB2603.

Formula F

| Ingredient | Amount (% w/w) |
|---|---|
| Terbinafine•HCl | 0.1 |
| PHMB | 0.3 |
| Ethanol | 20 |
| Distilled water | 79.6 |

The formulation of Formula F was placed in a spray bottle. Trials were then conducted by periodically spraying, over a 1-2 week period, the formulation on the toes of patients suffering from onychomycosis (and additionally tinea pedis in some cases). The treatments proved successful and successfully and quickly treated patients suffering from onychomycosis (and tinea pedis), without subsequent relapse.

Micro-Needle Patch

Transdermal patches have long been used for the administration of small-molecule lipophilic drugs that can be readily absorbed through the skin. This non-invasive delivery route is advantageous for the administration of many drugs incompatible with oral delivery, as it allows for direct absorption of the drug into the systemic circulation, by-passing both the digestive and hepatic portal systems which can also dramatically reduce the bioavailability of many drugs. Transdermal delivery also overcomes many of the challenges associated with subcutaneous injection by greatly reducing patient discomfort, needle anxiety, risk of accidental needle stick injury to the administrator and issues surrounding sharps disposal.

Despite these many advantages, transdermal delivery of drugs is confined to classes of molecules compatible with absorption through the skin. Delivery of small molecule salts and therapeutic proteins are not typically viable with traditional transdermal delivery, as the skin provides an effective protective barrier to these molecules even in the presence of absorption-enhancing excipients. However, micro-needle technology can be employed to deliver the nanoparticles containing antifungal agents directly to the epidermis, dermis and the nail matrix (where the nail and skin meet at the eponychium). By delivering the composition of the invention in this way, the nanoparticles will enter the nail matrix and capillary system and deliver the anti-fungal nanoparticle composition to the nail bed, under the hard nail plate, and into the fungi. In this way the potent antifungal agents can be directly delivered to the site of action thus reducing the treatment time and enhancing the potency.

FIGS. 14 and 15 show diagrams of a finger 10 to which a micro-needle patch (illustrated in FIG. 16) can be applied to a finger within the treatment area 12 shown by a dotted line. The treatment area 12 is formed of the dermis behind the nail 14 and also at the nail matrix (eponychium) 16 where the nail and skin meet. The nail root 18 is located in the area under the dermis behind the nail and can therefore be treated effectively by applying a micro-needle patch for delivering the composition of the present invention. Of course, the micro-needle patch could be used for toe nails in addition to finger nails.

FIG. 16 shows a diagram of a micro-needle patch which can be used to apply the composition of the present invention to an individual suffering from a fungal nail infection. The micro-needle patch 20 is formed of a flexible web of material 22 having an adhesive 24 applied to its underside. Centrally located on the underside of the flexible web is an array of downwardly extending micro-needles 26 having a plurality of points 30. The points can be formed as needles having conduits which are connected to a reservoir 28 containing the composition or simply have their points coated in the composition. In an alternative configuration, a reservoir 28 can expel the composition through holes disposed about the micro-needle arrays so that the composition can continuously coat the points of the array over a pre-determined time frame. It will be apparent to the skilled addressee that a number of different micro-needle patches are currently available and that the composition of the present invention could be adapted for use with a range of them.

The micro-needles, can be less than 2 mm in length, and preferably about 250 μm will be inserted into the skin with minimum patient discomfort and, given the small hole created, with minimal risk of post-injection infection, bleeding, or risk of inadvertent IV injection for an intradermal administration. In addition, micro-needles reduce risk to the injection administrator, as accidental puncture of the skin is nearly impossible with these small projections.

It is envisaged that the micro-needle patch could be used for a single treatment where all the patient has to do is remove the patch from a wrapper and apply it to the appropriate part of the finger or toe for a given period of time. In the alternative, the micro-needle patch could be sold in combination with the composition and the patient would coat a quantity of the composition onto the surface of the micro-needles and apply the patch to the body in the prescribed manner. The patch could come with markings on its exterior so as to assist the patient or physician correctly line up the micro-needles with the correct location on the finger or toe to be treated.

The forgoing embodiments are not intended to limit the scope of the protection afforded by the claims, but rather to describe examples of how the invention may be put into practice.

The invention claimed is:

1. A topical composition for use in the treatment of a fungal nail infection, the composition comprising nanoparticles, water, and ethanol, the nanoparticles formed of polyhexamethylene biguanide (PHMB) and terbinafine, or a derivative or salt thereof, wherein the composition comprises:

a) a ratio of terbinafine, or a derivative or salt thereof, to PHMB in the range of 1:2 to 1:4; and b) from 10% (v/v) to 30% (v/v) ethanol.

2. The composition as claimed in claim 1, wherein the terbinafine, or a derivative or salt thereof, is present at from about 5 to about 600 μg/ml.

3. The composition as claimed in claim 2, wherein the terbinafine, or a derivative or salt thereof, is present at from about 25 to about 200 μg/ml.

4. The composition as claimed in claim 2, wherein the terbinafine, or a derivative or salt thereof, is present at from about 50 to about 150 μg/ml.

5. The composition as claimed in claim 1, wherein the ethanol is present at from about 10% (v/v) to about 20% (v/v).

6. The composition as claimed in claim 1, wherein the PHMB is present at from about 150 to about 450 μg/ml.

7. The composition as claimed in claim 6, wherein the PHMB is present at up to about 300 μg/ml.

8. The composition as claimed in claim 1, wherein the water is present at about 70% to about 90% (v/v).

9. The composition as claimed in claim 8, wherein the water is present at up to about 80% (v/v).

10. A topical composition for use in the treatment of a fungal nail infection, the composition comprising nanoparticles and ethanol, the nanoparticles formed of PHMB and terbinafine, or a derivative or salt thereof, wherein:

(a) the terbinafine, or a derivative or salt thereof, is present in an amount in the range of 0.005% w/w to 1% w/w;

(b) the PHMB is present in an amount in the range of 0.015% w/w to 3% w/w;

(c) the ethanol is present at from about 10% (v/v) to 30% w/w; and (d) water is present at up to 90% w/w.

11. The composition as claimed in claim 10, wherein:
(a) the terbinafine, or a derivative or salt thereof, at 0.1% w/w;
(b) PHMB at 0.3% w/w;
(c) ethanol at 20% w/w; and
(d) water.

* * * * *